(12) United States Patent
Krespi

(10) Patent No.: US 8,679,103 B2
(45) Date of Patent: Mar. 25, 2014

(54) TWO STEP MAMMALIAN BIOFILM TREATMENT PROCESSES AND SYSTEMS

(75) Inventor: Yosef Krespi, New York, NY (US)

(73) Assignee: Valam Corporation, New York, NY (US)

( * ) Notice: Subject to any disclaimer, the term of this patent is extended or adjusted under 35 U.S.C. 154(b) by 726 days.

(21) Appl. No.: 12/642,021

(22) Filed: Dec. 18, 2009

(65) Prior Publication Data

US 2010/0160838 A1    Jun. 24, 2010

Related U.S. Application Data

(60) Provisional application No. 61/139,850, filed on Dec. 22, 2008.

(51) Int. Cl.
*A61B 18/18* (2006.01)
(52) U.S. Cl.
USPC .................... 606/16; 606/13; 606/2; 128/898
(58) Field of Classification Search
USPC ................................... 606/16, 13, 2; 128/898
See application file for complete search history.

(56) References Cited

U.S. PATENT DOCUMENTS

| | | | |
|---|---|---|---|
| 5,324,282 A | 6/1994 | Dodick | |
| 5,906,611 A | 5/1999 | Dodick | |
| 7,332,200 B1 * | 2/2008 | Soukos et al. | 427/554 |
| 2004/0224288 A1 * | 11/2004 | Bornstein | 433/224 |
| 2005/0261612 A1 * | 11/2005 | Hazan et al. | 601/46 |
| 2007/0043340 A1 | 2/2007 | Thyzel | |
| 2009/0054881 A1 | 2/2009 | Krespi | |
| 2009/0093865 A1 * | 4/2009 | Krespi et al. | 607/88 |

FOREIGN PATENT DOCUMENTS

| | | |
|---|---|---|
| WO | WO0067917 | 11/2000 |
| WO | WO200867361 | 12/2008 |

OTHER PUBLICATIONS

Soukos et al., "Photomechanical Drug Delivery into Bacterial Biofilms", Pharmaceutical Research, vol. 17, No. 4, 2000, pp. 405-409.
Soukos et al., "Photomechanical wave-assisted molecular delivery in oral biofilms", World J Microbial Biotechnol (2007) 23, pp. 1637-1646.
Krespi et al., "Laser Disruption of Biofilm", Laryngoscope 118, Jul. 2008, pp. 1168-1173.

* cited by examiner

*Primary Examiner* — Kinam Park
(74) *Attorney, Agent, or Firm* — K&L Gates LLP

(57) ABSTRACT

A two-step mammalian biofilm treatment process can have a first step of disrupting or dispersing an undesired biofilm present at a treatment site in or on a mammalian host by suitable mechanical action for example, by applying irrigation fluid, sonic or other vibration, a mechanical instrument or laser-generated mechanical shockwaves to the biofilm. The treatment can also have a second step comprising applying an antimicrobial treatment to the mammalian host to control possible infection related to biofilm dispersed in the first step or to residual biofilm at the treatment site. Usefully, the second step can be performed within a limited time period after the first step. The process can also include additional steps The antimicrobial treatment can employ light or an antibiotic material. Included are implants cleaned of biofilm by a described process.

29 Claims, 4 Drawing Sheets

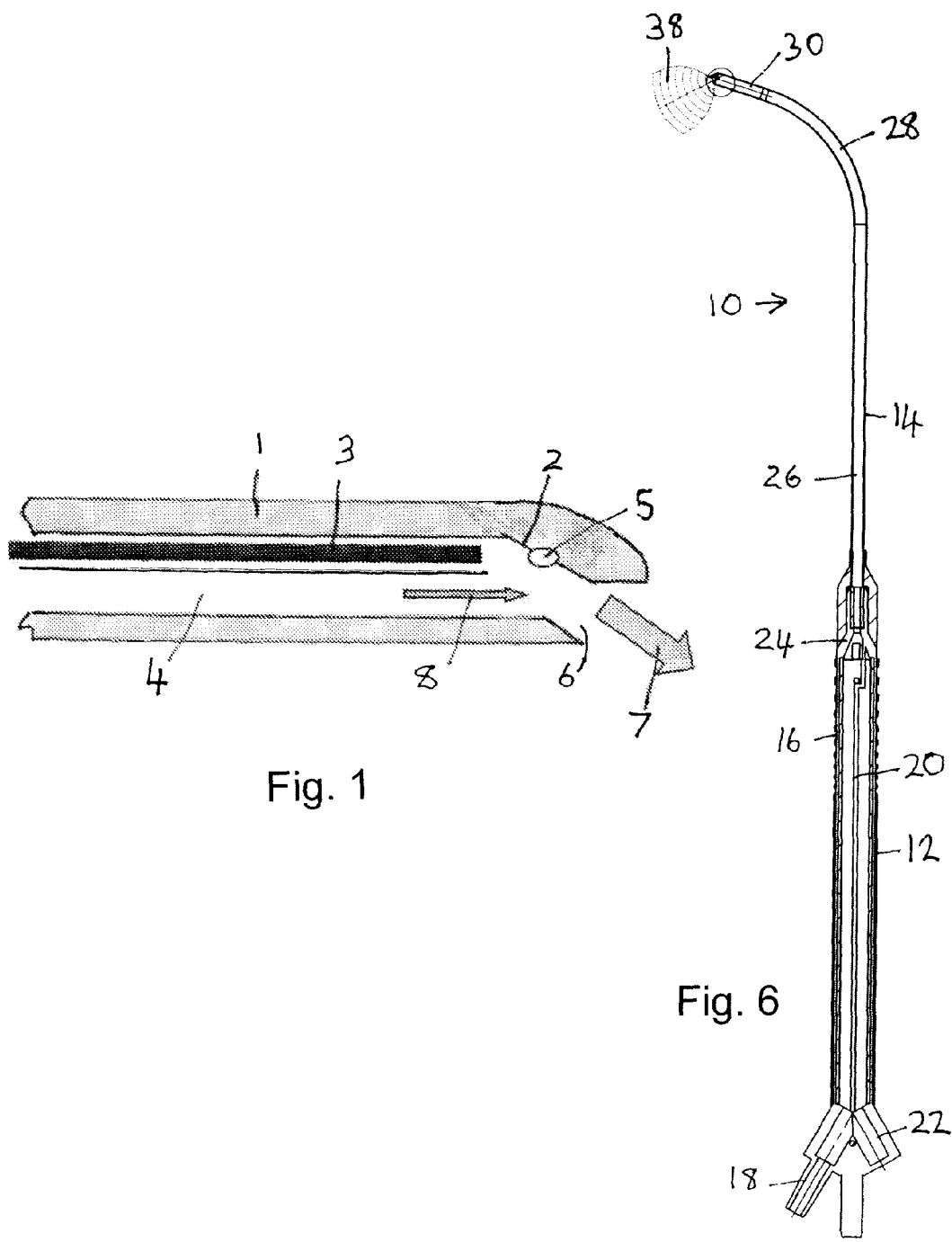

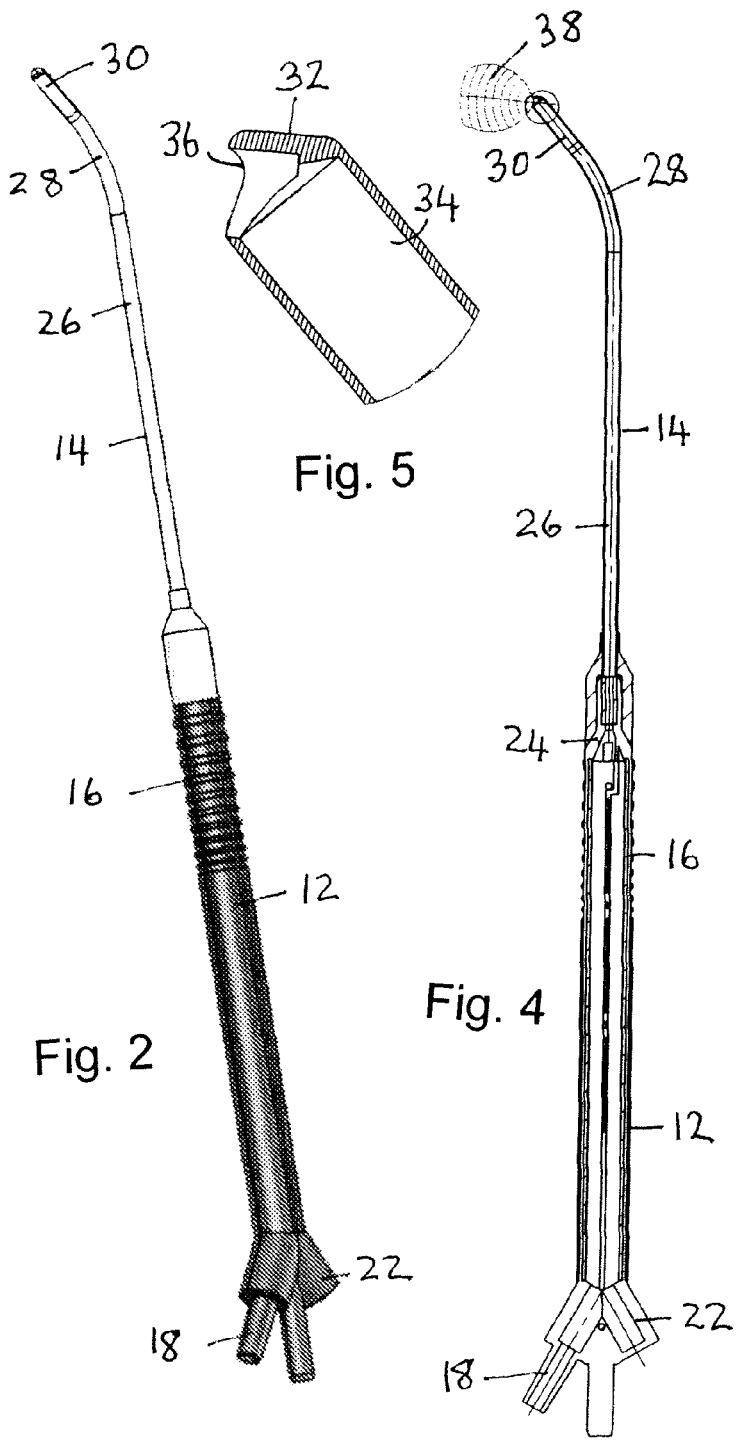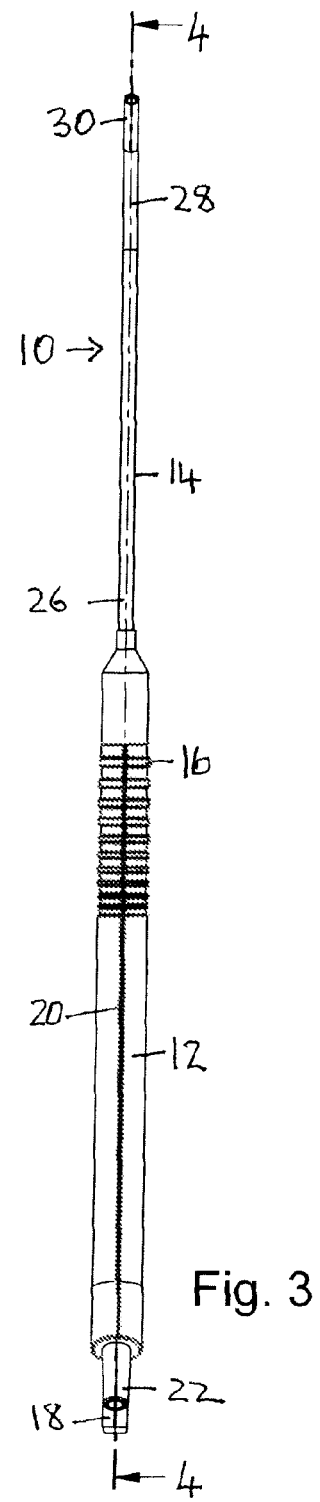

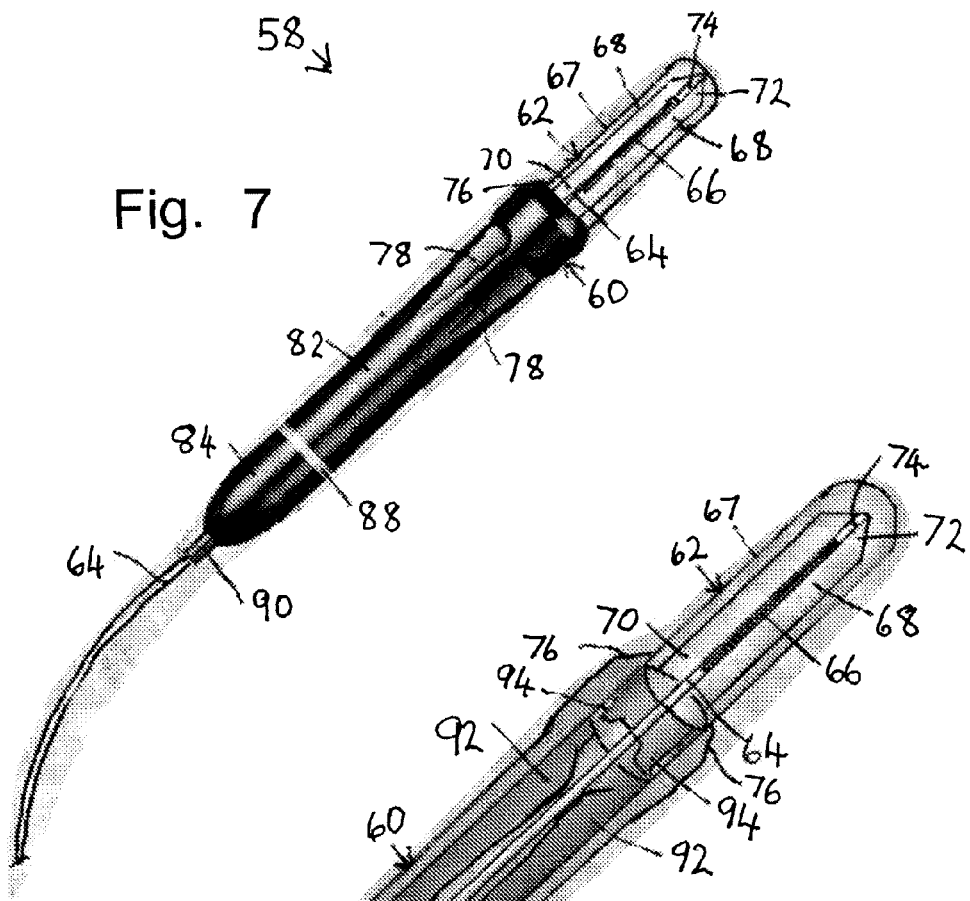
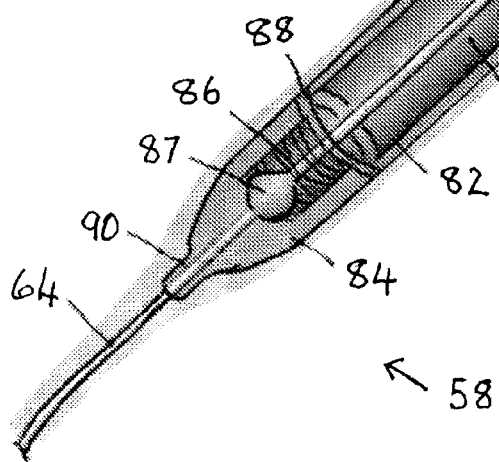
Fig. 7
Fig. 8

TWO STEP MAMMALIAN BIOFILM TREATMENT PROCESSES AND SYSTEMS

CROSS REFERENCE TO A RELATED APPLICATION

This application claims the benefit of provisional patent application No. 61/139,850, filed on Dec. 22, 2008, the entire disclosure of which is incorporated by reference herein.

STATEMENT REGARDING FEDERALLY SPONSORED RESEARCH OR DEVELOPMENT (Not applicable.)
The present invention relates to processes and systems for treating biofilms resident in mammals and provides processes and systems for treatment of undesired mammalian biofilms to control such biofilms and to reduce the probability of the reestablishment of same.

BACKGROUND

Biofilms are ubiquitous and can be problematic. Some examples of common biofilms include dental plaque, drain-clogging slime and the slippery coating found on rocks in streams and rivers.

Industrial and commercial problems attributable to biofilms include corrosion of pipes, reduced heat transfer and/or reduced hydraulic pressure in industrial cooling systems, the plugging of water injection jets and the clogging of water filters. In addition, biofilms can cause significant medical problems, for example, by infecting host tissues, by harboring bacteria that contaminate drinking water, and by causing rejection of medical implants.

Biofilms are generally formed when bacteria and/or other microorganisms adhere to surfaces in aqueous environments and begin to excrete a slimy, adhesive substance that can anchor the microorganisms to a wide variety of materials including metals, plastics, soil particles, medical implant materials and animal tissue.

A biofilm is often a complex aggregation of microorganisms comprising a protective and adhesive matrix generated by excretion of polymeric materials, for example, polysaccharides, from the microorganisms. Biofilms are often attached to surfaces, have structural heterogeneity and genetic diversity, and exhibit complex community interactions. Their protective matrix and genetic diversity mean that biofilms are often hard to destroy or otherwise control and conventional methods of killing bacteria, such as antibiotics, and disinfectants, are often ineffective against biofilms.

Because the single cell microorganisms in a biofilm typically are in an attached state, closely packed together and secured to each other and to a solid surface, they are more difficult to destroy than when they are in a free-floating mobile mode, as is the case in many mammalian infections.

A number of proposals have been made for the chemical or pharmaceutical treatment of, or regulation of, the growth of mammalian-resident biofilms. However, as implied above, such methods may be ineffective or subject to resistance or both, or may have other drawbacks commonly associated with pharmaceuticals such as systemic action and side effects.

Some suggestions for treatment of biofilms in humans appear in the patent literature. For example, Bornstein U.S. Patent Application Publication No. 2004/0224288 (referenced "Bornstein" herein) discloses a system and process for thermolytic eradication of bacteria and biofilm in the root canal of a human tooth employing an optical probe and a laser oscillator.

Also, Hazan et al. U.S. Patent Application Publication No. 2005/0261612 discloses a method for decreasing materials such as biofilm attached to a mammalian body which method includes attaching a nanovibrational energy resonator device onto an external or internal area of the body.

Oxley et al. "Effect of ototopical medications on tympanostomy tube biofilms." *Laryngoscope.* 2007 October; 117 (10):1819-24 describes experiments to examine the effect of ototopical medications on biofilms on fluoroplastic tympanostomy tubes. Reportedly, microbial activity in colony forming units (CFU) was decreased after three weeks. However, despite the treatment, the biofilm was not eradicated but continued to grow. The authors conclude that infectivity of the biofilm can be temporarily neutralized by antibiotic ototopicals and that the biofilm may progress despite treatment.

International patent publication No. WO 00/67917 describes a method for permeabilizing biofilms using stress waves to create transient increases in the permeability of the biofilm. As described, the increased permeability facilitates delivery of compounds, such as antimicrobial or therapeutic agents into and through the biofilm, which agents are apparently to be employed to treat the biofilm.

Desrosiers et al. "Methods for removing bacterial biofilms: in vitro study using clinical chronic rhinosinusitis specimens." Am J Rhinol. 2007 September-October; 21(5):527-32 describes an in vitro study on removed biofilms from bacterial isolates obtained from patients with refractory chronic rhinosinusitis. As described, the biofilm was treated with both static and pressurized irrigation and a citric acid/zwitterionic surfactant. According to the authors, the pressurized treatment employing irrigant and a surfactant can disrupt the biofilms tested.

Notwithstanding the foregoing proposals, it would be desirable to have new processes and treatments for treatment of biofilms resident in or on mammalian sites.

The foregoing description of background art may include insights, discoveries, understandings or disclosures, or associations together of disclosures, that were not known to the relevant art prior to the present invention but which were provided by the invention. Some such contributions of the invention may have been specifically pointed out herein, whereas other such contributions of the invention will be apparent from their context. Merely because a document may have been cited here, no admission is made that the field of the document, which may be quite different from that of the invention, is analogous to the field or fields of the present invention. Nor is any admission made that the document was published prior to, or otherwise predates, applicant's invention.

SUMMARY OF THE INVENTION

In one aspect, the present invention provides a combination two-step mammalian biofilm treatment process. The combination two-step process can comprise a first step of dispersing an undesired biofilm present at a treatment site in or on a mammalian host by mechanically shockwaves disrupting the biofilm and a second step. The second step can comprise applying an antimicrobial treatment to the mammalian host to control possible infection related to biofilm dispersed in the first step or to residual biofilm at the treatment site. Desirably, the second step is performed within a limited time period after the first step.

The processes of the invention can comprise one or more additional steps performed before the first step, after the second step or between the steps, if desired, for example a diagnostic step to identify the presence of a biofilm and optionally to biopsy and culture the biofilm to identify one or more microorganisms that are present.

By applying an antimicrobial treatment to control possible infection related to fragments or components of the biofilm that may have been dispersed in the first step the invention provides, in this aspect, a comprehensive mammalian biofilm process which offers the possibility of destroying or debilitating an existing biofilm and of reducing the probability of reestablishment or regrowth of the biofilm.

Desirably, the limited time period between steps is relatively short, for example about 48 hours, about 24 hours, about 3 hours, about 1 hour, about 30 minutes or about 10 minutes. In general, it can be expected that the more quickly the second step is performed, the more effective it will be in controlling possible reemergence of the biofilm.

The second, antimicrobial treatment step can be effected in any one of a variety of ways, for example by applying an antimicrobial dosage of light to the treatment site or by local or systemic administration of an antibiotic material to the mammalian host. Other suitable antimicrobial treatments will be or become apparent to a person of ordinary skill in the art.

Employing light, the second step can comprises diffusing the antimicrobial dosage of light onto the treatment site and in the vicinity of the treatment site and if desired can include applying an antimicrobial dosage of light to at least one other site on or in the mammalian host mammalian host that is subject to receiving material dispersed from the biofilm in the first step. Also, the antimicrobial dosage of light can reduce or otherwise control at least one species of the microorganisms in the biofilm.

Conveniently, infrared wavelengths of light can be employed for the antimicrobial dosage of light, optionally without use of a photosensitizer. However, visible energy wavelengths can be employed, if desired, optionally with use of a photosensitizer.

The biofilm can comprise matter foreign to the mammalian host, for example non-beneficial microorganisms and their exudates or other products, and the first step can comprise reducing the mass of, disrupting, attenuating or destroying the biofilm by the application of laser-generated mechanical shockwaves.

Usefully, the first step can comprise directing the mechanical shockwaves toward the biofilm at the treatment site. Also, the first step can comprise oscillating the biofilm by the application of the mechanical shockwaves.

Other methods can also be employed to perform the first step. For example, the first step can comprise mechanically disrupting the biofilm by performing one or more steps selected from the group consisting of applying laser-generated mechanical shockwaves to the biofilm, irrigating the treatment site; applying pressurized liquid to the biofilm; applying suction to the biofilm, applying sonic energy to the biofilm, applying ultrasonic energy to the biofilm; mechanically scraping or abrading the biofilm, and applying vibrations from a vibrational resonator device to the biofilm.

The biofilm can be attached to the treatment site, for example by microorganism exopolysaccharides, and the first step can comprise tearing one or more pieces of the biofilm away from residual biofilm at the treatment site or from the treatment site by applying the mechanical shockwaves.

Mammalian biofilms are often, or usually, undesired, and can sometimes lead to medical complications if not treated effectively. Accordingly, useful embodiments of the invention provide a simple and effective shockwave applicator that can be employed to disperse and help control internal or external mammalian treatment sites where biofilms are present. Internal treatment sites can be accessed via bodily cavities, for example the nostrils, or subcutaneously, employing a catheter, trocar or the like, or in other ways. A cooperative light applicator can be similarly tailored to apply an antimicrobial dosage of light to the targeted treatment site to provide a comprehensive biofilm treatment system designed to debilitate and reduce recurrence of one or more biofilms harbored at the treatment site. The light applicator can be configured for subcutaneous, catheter, trocar, nostril or other delivery of an antimicrobial dosage of light according to the nature of the desired treatment site.

In another aspect, the present invention provides a biofilm treatment system which can be used for performing a process according to the invention, or for other purposes, if desired. The biofilm treatment system can comprise a shockwave applicator configured to apply the mechanical shockwaves to the biofilm and a light applicator comprising a light source, the light applicator being operable to apply an antimicrobial dosage of light to the treatment site.

Shockwaves or pressure pulses to be applied to the treated biofilm by the shockwave applicator can be generated using light energy, for example, light energy output by a laser, or by other suitable means, or the shockwaves can be generated in another suitable manner.

Any suitable shockwave applicator can be employed. If desired, the shockwave applicator can be configured to output shockwaves in a shockwave pattern extending forwardly of the distal end of the shockwave applicator to facilitate directing the shockwaves toward the treatment site.

One exemplary shockwave applicator useful in the practice of the invention comprises an ionizable target for transducing laser energy into shockwaves and an optical fiber extending along the shockwave applicator. The optical fiber can have a distal end positioned adjacent the ionizable target and can be connectable with a pulsed laser energy source to receive pulses of laser energy from the laser energy source and discharge the pulses of laser energy from the distal end of the optical fiber to impinge on the ionizable target, thereby outputting shockwaves.

Also, any suitable light source can be employed for the light applicator. Usefully, the light source can be capable of outputting light at a wavelength in a range of from about 400 nm to about 1500 nm. For example, the light source can be capable of outputting infrared light at a wavelength in a range of from about 850 nm to about 950 nm. The light source can comprise a laser, a laser diode, a light-emitting diode, a gas discharge lamp, a flash lamp or a high intensity pulsed light.

While the invention is not limited by or dependent upon any particular theory, it appears from such experiments that the shockwaves employed may be sufficiently powerful to break up a biofilm, and possibly dislodge it from its support structure, without causing visible damage to the underlying tissue, implant or other host structure. Also, the shockwave applicator can propagate little or no laser energy externally of the instrument. The shockwave applicator can include means for irrigation of the treatment site, or both, to remove detritus from the shockwave applicator and/or the treatment site, if desired. An aqueous fluid can be employed for irrigation. Optionally, the aqueous fluid can be pulsed.

Biofilms that can be treated by a process according to the invention may be resident or on or at any of a variety of anatomical sites and include biofilms secured to the treatment site by polysaccharide material. The biofilms can comprise one or more microorganisms such for example as bacteria, fungi, protozoa, archaea, algae and/or microscopic parasites.

It is believed that shockwaves generated by certain shockwave applicator embodiments of the invention can oscillate some biofilms resident on various substrates and cause pieces of the biofilm to tear away. In some cases a biofilm can be more or less completely removed from its site of residence.

The invention includes mammalian host implants cleaned of biofilm by a treatment process according to the invention.

In another aspect, the invention provides a new use of a biofilm treatment system comprising a shockwave applicator including an ionizable target for transducing laser energy into shockwaves and an optical fiber having a distal end positioned adjacent the ionizable target and being connectable with a pulsed laser energy source to receive pulses of laser energy from the laser energy source and discharge the pulses of laser energy from the distal end of the optical fiber to impinge on the ionizable target to generate and output shockwaves for treating mammalian resident biofilm by application of the shockwaves to the biofilm and comprising a light applicator for applying an antimicrobial dosage of light energy to a mammalian treatment site harboring the biofilm.

BRIEF DESCRIPTION OF THE SEVERAL VIEWS OF THE DRAWING

Some embodiments of the invention, and of making and using the invention, as well as the best mode contemplated of carrying out the invention, are described in detail herein and, by way of example, with reference to the accompanying drawings, in which like reference characters designate like elements throughout the several views, and in which:

FIG. 1 is a schematic view of laser generation of shockwaves from the distal tip of a shockwave applicator useful in the practice of the invention;

FIG. 2 is a perspective view of an embodiment of a shockwave applicator according to one embodiment of the invention which can be useful as a shockwave applicator for applying shockwaves to treat biofilms at sinus and other locations;

FIG. 3 is a front view of the shockwave applicator shown in FIG. 2;

FIG. 4 is section on the line 4-4 of FIG. 3;

FIG. 5 is an enlarged view of the tip of the shockwave applicator shown in FIG. 4;

FIG. 6 is a view similar to FIG. 4 of another embodiment of shockwave applicator component according to the invention;

FIG. 7 is a schematic perspective view of an embodiment of a light applicator according to one embodiment of the invention which can be useful for applying a dosage of antimicrobial light to a treatment site harboring a biofilm or biofilm remnants; and FIG. 8 is an enlarged view of the nasal light applicator shown in FIG. 5, showing some internal structure thereof.

DETAILED DESCRIPTION OF THE INVENTION

Figure 1A:
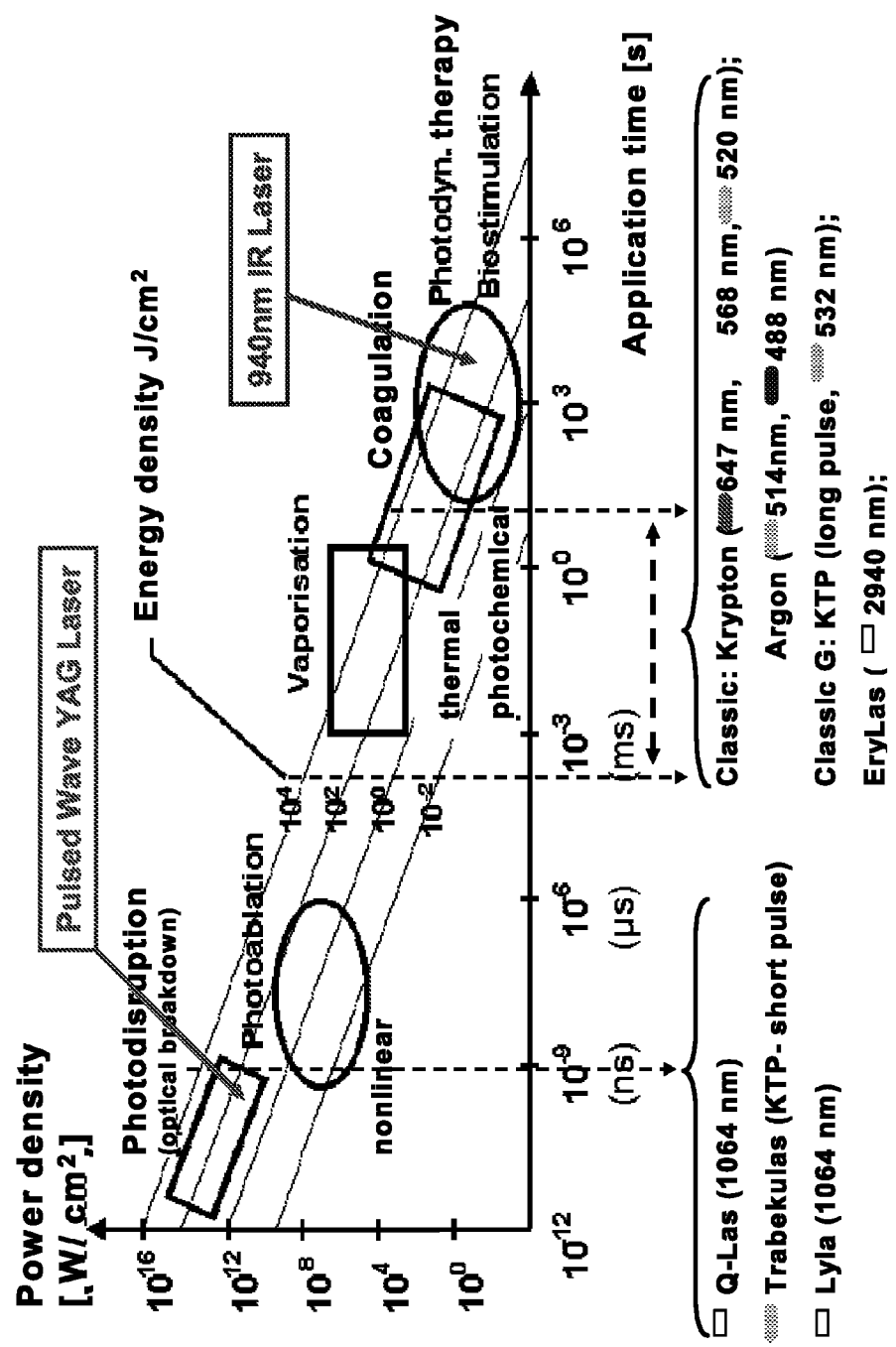
FIG. 1A is a graph showing schematically the effects of various laser treatments that are generally obtainable at different power densities, energy densities and application times.

U.S. patent application Ser. No. 12/139,295, the disclosure of which is incorporated by reference herein, describes and claims a process for treating biofilms wherein shockwaves are applied to a biofilm to disperse it. In vitro data described in that application demonstrate a shockwave treatment causing a biofilm to oscillate, tearing and disintegrating the biofilm and substantially removing the biofilm from a site of attachment such as a bundle of sutures, an orthopedic screw or a tympanostomy tube.

The present invention provides a comprehensive process for treating biofilms which aims to both disperse a biofilm present at a treatment site and to reduce the probability of the biofilm reforming or regenerating. As described herein the invention includes a two-step mammalian biofilm treatment process comprising dispersing an undesired biofilm present at a treatment site in or on a mammalian host by applying laser-generated mechanical shockwaves to the biofilm and a second step of applying an antimicrobial treatment to the mammalian host to control possible infection related to biofilm dispersed in the first step. Desirably, the second step can be performed soon after the first step. In another embodiment of the invention the second step can be performed more or less simultaneously with the first step. In general, the shockwave treatment processes described in patent application Ser. No. 12/139,295 can be employed for practicing the first step of the processes described herein and shockwave applicators or instruments are useful as shockwave applicators in system aspects of the present invention. Other processes and devices can alternatively be used for performing the first step, as is described herein or as will be known or apparent to a person of ordinary skill in the art, in light of this disclosure, or will become known or apparent in the future, as the art develops International Publication No. WO 2008/067,361, the disclosure of which is incorporated by reference herein describes light application methods and light applicators which can be employed in practicing the second step of process aspects of the present invention or as light applicators in practicing system aspects of the present invention.

The antimicrobial treatment can comprise any suitable measure for example administration or application of an antimicrobial dosage of an antibiotic substance or composition or of light at a suitable wavelength.

For treatment of biofilms that potentially may comprise antibiotic-resistant microbes, the invention provides a biofilm treatment system comprising a mechanical shockwave applicator to disperse the biofilm and a light applicator to provide an antimicrobial treatment to control possible residual biofilm at the treatment site or dispersed biofilm fragments or organisms, and to inhibit reestablishment or regeneration of the biofilm at the treatment site or elsewhere.

Desirably, in some cases, light energy can be employed at infrared wavelengths to provide a simple antimicrobial treatment not requiring use of photosensitizers, stains, colorants or the like at the target site.

The light energy can include ultraviolet wavelengths, if desired. However, considerable care will likely be needed to avoid tissue damage when employing ultraviolet light energy. Thus, the invention also provides treatment processes which avoid use of ultraviolet light.

If desired an antibiotic compound or composition can be administered systemically or locally, or both systemically and locally, to provide an antimicrobial treatment which is alternative or adjunctive to the use of light, where antibiotic resistance is not a concern.

The invention can provide a biofilm treatment system comprising a shockwave applicator and a light applicator that are cooperative to provide a comprehensive treatment of a particular bodily site harboring a biofilm or of a biofilm-implicated condition. For example, the shockwave applicator can have an output proximally mounted on an extended reach needle or the like to access internal treatment sites such as a sinus cavity through a body opening such as a nostril and the light applicator can be configured to apply a suitable dosage of light energy through the same opening, the nostril to reach the same treatment site, the sinus cavity. Desirably the light applicator can also spread the light around the nostril and the posterior nasal cavity, being locations where dispersed biofilm fragments could potentially lodge and reestablish themselves. In another example, both the shockwave applicator and the light applicator can both be adapted for insertion into a body opening, for catheter delivery, or trocar use to access a treatment site subcutaneously or through a bodily lumen, for example the vasculature or to access a bodily cavity, or in other suitable manner.

The shockwave applicator can be capable of outputting high energy shockwave pulses of short duration and directing them to a specific structure or area, for example a biofilm or an anatomical, prosthetic or implant structure supporting the biofilm. Surprisingly, high energy shockwave pulses can be applied and a biofilm can be broken up, dispersed or destroyed with little if any damage to underlying or surrounding tissue. The light applicator can be capable of being employed to spread light if desired, flooding or bathing an area including and extending beyond the footprint of the biofilm to reach other locales where biofilm fragments may be present and target these areas with an antimicrobial dosage of light.

Biofilms can form in mammalian hosts when bacteria adhere to a wet surface and begin to excrete a slimy, glue-like substance that can anchor the bacteria to tissue or medical implants. Such biofilms can comprise many types of bacteria, fungi, debris and corrosion products. Biofilms encountered in the human or other mammalian body generally comprise matter which is foreign to the mammalian host. Generally, biofilms do not comprise host tissue and are not useful components of the mammalian host. Thus, embodiments of the invention may apply treatments to host tissue on which biofilm resides or which are in the vicinity of biofilms but generally do not aim to change or modify the host tissue or other host structure subject to treatment. One embodiment of the invention comprises controlling or attenuating biofilm foreign matter while leaving host tissue intact. Useful embodiments of the invention target biofilms which may actively or passively adversely affect normal functioning of the mammalian host.

Non-living surfaces in the body, for example catheters, contact lenses, artificial joints and other medical devices may be more prone to biofilm formation than living tissue. However, biofilms can also grow on living tissue, and may cause diseases such as endocarditis, lung, dental, sinus, ear and other infections. For example, it is believed that biofilms may play an etiologic role in chronic otolaryngologic infections. Therapeutic methods designed to treat acute infections caused by surface or floating (planktonic) microorganisms may be found to be ineffective for chronic infections when biofilms are present.

Bacteria can adhere to solid surfaces and excrete a slimy, slippery coat with structured features. The resulting adherent mass can be referred to as a bacterial biofilm. The formation of biofilm structure occurs in multiple stages. First the bacteria may attach to a convenient, usually wet, surface. The attachment may be strengthened by a polymeric matrix adhering densely to the surface, and an aggregation of micro colonies occurs. The environment can provide growth and maturation for the biofilm which becomes an organized structure. Finally, during its mature phases, the biofilm may detach, disperse or embolize to perform the same cycle in adjacent or distant areas.

The composition of a biofilm can comprise, for example, about 15% by weight of bacteria cells and about 85% by weight of 'slime'. The slimy environment also appears to protect the bacteria from natural host defenses such as inflammatory cells, antibodies and antimicrobial treatments. As the biofilm cells consume nutrients from surrounding tissue and fluids, nutrient gradients develop until bacteria near the center or centers of the biofilm become starved and go into quiescent state. It is speculated that this dormancy may partially explain the resistance often displayed by biofilm bacteria to antibiotics which are effective against rapidly growing bacteria in standard tests. The biofilm bacteria survive in a matrix rich in extracellular polymeric substances ("EPS" herein) including polysaccharides, nucleic acids and proteins providing a protective and nutritious environment to the microorganisms.

Some examples of virulent bacteria that may be found in biofilms treatable by the processes and systems of the invention, with diseases with which they are associated indicated in parenthesis, are: *Pseudomonas aeruginosa* (cystic fibrosis); *Staphylococcus aureus* (osteomyelitis); *Proteus vulgaris* (pyelonephritis); *Streptococcus viridans* (endocarditis); culture-negative prostatitis; and *Haemophilus influenzae* (otitis media).

It is also believed that a biofilm can have a complex morphology comprising communication channels in which cells in different regions of the biofilm exhibit different patterns of gene expression. It may have a three dimensional architecture with open channels that allow the transport of nutrients into the biofilm. Furthermore, bacteria in biofilms may communicate through quorum sensing molecules that can coordinate and up-regulate virulence factors when cells became starved. Quorum sensing, or exchange of molecules, genes, DNA and free communication between cells, can provide the bacteria within the biofilm a resistant and protective environment. Known anti-bacterial agents may require a hundred- or thousand-fold 'normal' antibiotic dosage to be effective against such resistant biofilm structures; which is not feasible to administer systemically owing to toxicity.

Biofilms can provide a mechanism for microorganisms to survive extreme temperature changes, radiation or mechanical trauma. Antibiotics may eradicate planktonic (floating or drifting) microorganisms, and possibly also surface bacteria on a biofilm without damaging bacteria protected within the polymer matrix. This understanding may point to a role of biofilms in the etiology of chronic infections with acute exacerbations. Some examples in otolaryngology include chronic rhinosinusitis, chronic otitis media, adenoiditis and cryptic tonsillitis. A given condition may be aggravated by the presence of a prosthetic, implantable device or catheter for example a tympanostomy tube, a tracheotomy tube, a cochlear implant, a stent, packing material or a foreign body. Biofilms preferentially form in grooves, depressions, pockets and other surface discontinuities on host-resident medical devices and implants. Biofilms can also form between or on the fibers of sutures, on cuffs and in the mesh-like structures of knitted or woven grafts. The literature reports having found a dense biofilm in the surface depressions of a cochlear implant removed from a patient with an intractable infection. These and other sites where biofilms are attached, resident or supported can constitute treatment sites to be subjected to shockwave treatments in embodiments of the processes of the present invention.

Not all biofilms are pathogenic. However even non-pathogenic biofilms can create an inflammatory reaction in surrounding host tissue and may cause collateral damage through cytotoxic, proteolytic, and proinflammatory effects. These effects may cause localized tissue reactions and recurrent infections. Sometimes, the host response to a biofilm can result in severe and sustained inflammation. For example, in diseases such as cystic fibrosis and gingivitis, if the neutrophils fail to engulf the bacteria inside biofilms, they may degranulate and damage host tissues.

The processes of the invention described herein usefully can be employed in the treatment of biofilms resident in mammals, including in particular, humans. In addition, these processes can be applied to treatment of non-human mammals including, for example, horses, cattle, sheep, llamas, husbanded animals, pets including dogs and cats, laboratory animals, for example, mice, rats and primates, animals employed for sports, breeding, entertainment, law enforcement, draft usage, zoological or other purposes, if desired. The processes and devices of the invention are not limited by the theories of biofilm formation and structure described herein or by any other theories.

Processes according to the invention can be employed to treat biofilms resident at, adhered to, or otherwise present at any of a variety of anatomical sites, including any one or more sites selected from the group consisting of otolaryngological sites; nasal, sinus, and middle ear cavities; pharyngal, tonsillar, dental and periodontal sites; toenails, fingernails and their environment; wound closure devices and materials, sutures, sites on cardiac implants, endovascular implants, orthopedic implants, gynecological implants, intrauterine devices, urologic implants, urinary catheters, therapeutic and other implants as will be or become apparent to a person of ordinary skill in the art. The invention provides treatment systems adapted to treat a biofilm present at any one or more of the foregoing sites by a process according to the invention.

The invention includes embodiments wherein the biofilm can be present at a treatment site selected from the group consisting of the sinuses, the sinuses accessible via the nasal cavity, the frontal, ethmoidal, sphenoidal and maxillary sinuses, otological sites, upper nasal, and middle ear cavities.

The biofilm treatment processes of the invention can provide a comprehensive approach to complete or partial elimination of, attrition of, removal or reduction of, destruction of or other desired control of, or biofilm resident in or on a host mammal, in particular, a human being, and prevention of its recurrence. Processes according to the invention can treat undesired biofilms which may cause the host to be symptomatic and in some cases can lead to medical complications.

As summarized above the invention provides biofilm treatment processes which comprise mechanically disrupting or a biofilm resident at a treatment site on or in a mammalian host, followed by an antimicrobial treatment.

Mechanical disruption can comprise a process which physically breaks up a biofilm, disturbs, disrupts or subverts the protective layer or layers of the biofilm which may inhibit antimicrobial treatments or otherwise physically treats the biofilm to render the microbial components of the biofilm more susceptible to reduction or attenuation by an antimicrobial such as a pharmaceutical agent or antimicrobial radiation, which radiation treatment optionally can be enhanced by a sensitizer.

As described herein mechanical disruption can be effected in any one or more of a variety of ways. By way of example, the application of laser-generated mechanical shockwaves to the biofilm is described in detail herein.

Alternative methods for mechanically disrupting the biofilm include irrigating the treatment site; applying pressurized liquid to the biofilm; applying suction to the biofilm, applying sonic energy to the biofilm, applying ultrasonic energy to the biofilm; mechanically scraping or abrading the biofilm, applying vibrations from a vibrational resonator device to the biofilm and other methods as will be known or apparent to a person of ordinary skill in the art, in light of this disclosure, or will become known or apparent in the future, as the art develops.

Irrigating the treatment site can be effected in any suitable manner, for example by manipulating a probe or other suitable instrument coupled to a source of saline, or other suitable pressurized fluid, generally, but not necessarily, a liquid, to direct a flow, optionally a pressurized jet of irrigation fluid at the biofilm. If desired, the fluid flow can be moved around to impact different parts of the biofilm by suitable manipulation of the irrigation instrument.

Alternatively, or in addition, suction can be to the biofilm, in a comparable manner, employing a manipulatable instrument coupled to a suction source.

If desired, sonic or energy can be applied to the biofilm employing a sonic energy generating device. The sonic energy can be transmitted from the sonic energy generating device, radiatively or conductively, or in another suitable manner. For example, sonic energy can be output from the generating device and directed at the biofilm treatment site to travel through an intervening fluid medium or fluid media, to the biofilm treatment site. Alternatively, the generating device can be contacted with a suitable available portion of the patient's anatomy and conducted through the patient's skin, bone, tissue, or other anatomy to the biofilm treatment site.

Ultrasonic, or other vibrational or microvibrational energy can be applied to the biofilm in a comparable manner to that described for sonic energy, employing a suitable ultrasonic, or other vibrational or microvibrational energy generating device which can optionally be a resonator device or other suitable energy generating device.

Mechanically scraping or abrading the biofilm, can be effected by suitable manipulation of a probe configured with a suitable scraper or abrader tip. Optionally, the probe tip can have a sharp, dull or blunt blade or the like for scraping, or a suitably configured abrasive surface, or another suitable configuration.

In any mechanical disruption method, if desired, and if practicable, the applied disruptive force can be moved around the biofilm or the biofilm treatment site to impact different parts of the biofilm by suitable manipulation of the instrument or other device employed to apply the disruptive force.

In one embodiment of the invention, employing shockwaves, the shockwaves generated are non-convergent shockwaves and the process can comprise directing the non-convergent shockwaves on to the biofilm resident at the treatment site.

Biofilms can comprise a wide variety of microorganisms, for example, one or more microorganisms selected from the group consisting of an antibiotic-resistant microorganism, methicillin-resistant *Staphylococcus aureus*, antibiotic-resistant *Staphylococcus aureus*, antibiotic-resistant alpha-hemolytic streptococci, antibiotic-resistant *Streptococcus pneumoniae*, antibiotic-resistant *Haemophilus influenzae*, antibiotic-resistant coagulase-negative *Staphylococci*, *aspergillus, candida* and *penicillium* families, *mycoplasma, alternaria, Chlamydia*, antifungal-resistant *aspergillus*, antifungal-resistant *candida* and antifungal-resistant *penicillium* families, antifungal-resistant *mycoplasma, alternaria* and antifungal-resistant *Chlamydia*.

The first, shockwave application step of a process according to the invention can comprise impinging a pulsed laser beam on to an ionizable target to generate non-convergent pulses of mechanical shockwaves. For example, the first step can comprise pulsing laser energy impinged on the target to have one or more pulse characteristics selected from the group consisting of a pulse width in the range of from about 2 ns to about 20 ns, a pulse rate of from about 0.5 Hz to about 200 Hz, a pulse energy in a range of from about 2 mJ to about 15 mJ of energy per pulse, and a fiber-to-target distance in the range of from about 0.7 to about 1.5 mm.

The antimicrobial treatment comprises applying to the biofilm a dosage of light having a wavelength of from about 400 nm to about 1500 nm, for example a dosage of light having a wavelength in the range of from about 600 nm to about 1200 nm.

Another example of the antimicrobial treatment comprises applying to the biofilm a dosage of light having a wavelength in the range of from about 800 nm to about 1200 nm and the light dosage is applied without applying colorant or photosensitizer material to the treatment site.

A further example of the antimicrobial treatment comprises applying to the biofilm a dosage of light having a wavelength in the range of from about 850 nm to about 950 nm and the light dosage is applied without applying colorant or photosensitizer material to the treatment site.

A still further example of the antimicrobial treatment comprises applying to the biofilm a dosage of light having a wavelength in the range of from about 400 nm to about 700 nm and applying to the biofilm a colorant selected to absorb the dosage of light or a photosensitizer material.

The light dosage can be applied at an energy of from about 1 mW to about 200 mW for a duration sufficient to deliver from about 0.2 to about 20 Joules of energy. For example, the light dosage can be applied at an energy intensity of from about 10 mW to about 100 mW for a duration sufficient to deliver from about 2 to about 10 Joules.

The treatment site can comprise a sinus or posterior nasal site or other sinonasal site, and the biofilm can be present at the sinus or posterior nasal site and the second step comprises flooding the nasal cavities with a diffuse antimicrobial dosage of light.

Where the treatment site comprises a sinonasal site, the second step can comprise applying an antimicrobial light dosage to each anterior nasal cavity of the mammalian host and, optionally, depending upon the wavelength of light employed, applying a colorant to the anterior nasal cavity to sensitize infectious microorganisms present in the anterior nasal cavity to the microorganism-reducing light.

The light dosage of microorganism-reducing light can be applied to each nasal vestibule of the mammalian host. The antimicrobial treatment can comprise inserting a light-diffusing nasal dilator through a naris of the mammalian host to dilate the nostril of the mammalian host and delivering the light dosage through a fiber optic tip located within the nasal dilator and through the nasal dilator to the anterior nasal cavity of the mammalian host.

The biofilm treatment process can be repeated as desired, for example at one or more intervals of from about 1 to about 7 days.

The biofilm treatment system can comprise a light applicator having a light source comprising an optical fiber and a diffuser to diffuse light emitted from the optical fiber. The light applicator comprises a hand piece to enable a user to manipulate the light applicator and the hand piece can be removably attachable to the optical fiber.

The light applicator can be insertable into a bodily cavity of the mammalian host to apply the light dosage within the bodily cavity.

In one example, the light applicator is configured for applying light to the interior nasal anatomy of the mammalian host and comprises a light output member to deliver light within the nose and a hollow light-transmissive, light diffusing nasal dilator insertable through a naris of the treatment mammalian host to dilate the nose, wherein the light output member can be accommodated in the hollow interior of the nasal dilator to deliver light to the interior nasal anatomy through the nasal dilator.

A shockwave applicator useful in practicing process aspects of the invention or in a biofilm treatment system according to the invention can be capable of generating pulsed laser energy having one or more pulse characteristics selected from the group consisting of a pulse width in the range of from about 2 ns to about 20 ns, a pulse rate of from about 0.5 Hz to about 200 Hz, a pulse energy in a range of from about 2 mJ to about 15 mJ of energy per pulse.

One example of a suitable shockwave applicator comprises a needle portion supporting the ionizable target and optical fiber, the needle portion comprising an elongated proximal section to reach into a bodily cavity and a distal tip disposable in a bodily cavity to output shockwaves generated by the shockwave applicator.

The needle portion can comprise a curved section between the distal tip and the elongated proximal section. The curved section can orient the distal tip to address a treatment site, the distal tip optionally being oriented at an angle in the range of from about 40° to about 60° or in the range of from about 10° to about 25° to the longitudinal axis of the proximal section. The distal tip can comprise a distally elongated straight section and a generally triangular cross-section along the length of the distally elongated straight section.

The distally elongated straight section of the distal tip comprises a distally elongated flat or convex target surface and the shockwave applicator optical fiber comprises a fiber end disposed to impinge laser energy on the target surface to generate shockwaves and wherein the target surface is oriented to project the shockwaves in a limited geometric volume forwardly of the distal tip and angled to the axis along the distal tip straight section on the same side of the axis as proximal section. And the distally elongated straight section can comprise a heat sink. Other configurations will be apparent for application to other host treatment sites.

If desired, a biofilm treatment system according to the invention can further comprise an endoscope for viewing the treatment site, the shockwave applicator and endoscope being configured for the application of shockwaves to the treatment site to be modified in response to a view of the treatment site wherein, optionally, the shockwave applicator and endoscope are configured for insertion into the mammalian host to treat biofilms at non-ophthalmologic sites.

Some embodiments of process according to the invention can comprise controlling the biofilm non-thermolytically or by avoiding delivery of heat to the treatment site or without applying stain to the biofilm or according to a combination of two or all of the foregoing parameters. In other embodiments, the process can comprise controlling the application of shockwaves to maintain host tissue at the treatment site intact or free of symptoms of heat or other damage or both intact and free of symptoms of heat damage.

In some cases a single treatment can be effective to provide adequate destruction, disruption or dispersal of the biofilm. Multiple passes may be employed in the course of a single treatment. In some embodiments of the invention an individual treatment wherein shockwaves are being applied to a biofilm can be performed in less than five minutes and the interval during which shockwaves are applied to the biofilm can be no more than two minutes or, possibly, one minute. During this interval, a desired number of shockwave pulses can be targeted at the biofilm, which number can be in the range of from about 5 to about 100 pulses, for example in the range of from about 10 to about 50 pulses. In some cases such a single treatment can more or less completely disrupt, disperse or destroy the biofilm.

The invention also includes processes wherein a biofilm infection or infestation is treated repeatedly at intervals, for example, of from about four hours to about a month. The treatments can, if desired be repeated at intervals of from about 1 to about 14 days. Treatments can be repeated until adequate control of the biofilm, and of recurrence of the biofilm, are obtained, if desired. A course of treatment can, for example, endure for from about two weeks to about twelve months or for another suitable period.

The term "shockwave" as used herein is intended to include unsteady pressure fluctuations or waves having a speed greater than the speed of sound. Also included are pressure waves having a speed greater than the speed of sound which comprise a disturbed region in which abrupt changes occur in the pressure, density, and velocity of the medium through which the pressure wave is traveling.

The processes of the invention can employ any suitable shockwave applicator which can apply shockwaves, pressure pulses or other suitable non-chemical mechanical or energetic forces to mammalian biofilms to destroy them partially or completely, without unacceptable damage to host tissue, for example, so that the tissue at the treatment site remains intact. The energetic forces can be generated by laser or other photic means, piezoelectrically or in another desired manner.

Some examples of shockwave applicators suitable for the practice of the present invention include surgical instruments such as are disclosed in Dodick et al. U.S. Pat. Nos. 5,906,611 and 5,324,282 (referenced as "the Dodick instrument" herein). The disclosure of each of the Dodick et al. patents is incorporated by reference herein. Some uses and modifications of the Dodick instrument which also can be useful in the practice of the present invention are disclosed in Thyzel U.S. Patent Application Publication No. 2007/0043340 (referenced as "Thyzel" herein). The disclosure of Thyzel is also incorporated by reference herein.

As described by Dodick et al., the Dodick instrument is a laser-powered surgical instrument that employs a target for transducing laser energy into shockwaves. The instrument can be used in eye surgery, particularly for cataract removal which can be effected by tissue fracturing. The Dodick instrument can comprise a shockwave applicator holding a surgical needle and an optical fiber extending through a passageway in the needle. An open distal aspiration port for holding tissue to be treated communicates with the passageway through the needle. An optical fiber can extend along the length of the needle and have its distal end positioned close to a metal target supported by the instrument. Also as described by Dodick et al., pulses of laser energy are discharged from the distal end of the optical fiber to strike the target. The target, which can be formed of titanium metal, is described as acting as a transducer converting the electromagnetic energy to shockwaves that can be directed onto tissue in an operating zone adjacent to the aspiration port. If desired, the needle can be flexible to enhance access to treatment sites.

As described in the literature, such laser generated shockwave technology can be used in cataract surgery for extraction and photolysis of the lens and for the prevention of secondary cataract formation. The technology can be used in surgical methods which gently break-up the cloudy lens into tiny pieces that can be removed through an aperture of the probe. Using several hundred pulses, resulting in high pressures the object can be cracked efficiently with low energy deposition and without significant temperature changes around the needle.

According to M. Iberler et al. "Physical Investigations of the A.R.C.-Dodick-Laser-Photolysis and the Phacoemulsification", unlike ultrasonic energy cataract treatments, this type of instrument produces no clinically significant heat at the incision site, when employed for cataract surgery. Apparently, the heat created within the tip of the instrument can be dissipated by heat transport in the solid titanium target.

Some embodiments of the present invention can employ the shockwaves generated at the instrument's distal port, to impinge on and destroy, attenuate, disrupt or dislodge a host-resident biofilm attached to host tissue, to an implant surface or to another treatment surface located in the operating zone adjacent the shockwave applicator's distal port. The process can be performed with or without aspiration through the shockwave applicator's distal port or through another port in the shockwave applicator or another device.

The shockwaves output can be directed at a biofilm or other target, and in some embodiments of the invention can be applied in an identifiable approximate pattern such as a circle, an ellipse or a comparable shape, or a portion of such a pattern. The shockwaves can be output as a non-convergent shockwave beam confined to be directional. For example the shockwave beam can be divergent and can have a generally conical or other suitable shape. The divergence of the shockwave beam, defined by opposed outer edges of the beam can be from about 0° to about 90° for example from about 5° to about 30°. Such a non-convergent shockwave beam can be useful for controlled application of shockwaves on selected areas of a treatment site.

While the invention is not limited by any particular theory, it is believed that the application of mechanical shockwaves or other pressure pulses will burst the cell walls of at least some of the organisms in the treated biofilm, destroying the organisms. Unlike chemical or pharmaceutical processes which may have little effect on dormant organisms that may have very low metabolic rates, the shockwaves employed are expected, in some cases, also to destroy such dormant organisms that receive the full effect of a shockwave output from the shockwave applicator. Destruction of organisms that are actually or potentially resistant to antibiotics is contemplated to be achievable, in some cases. Accordingly, in some cases where the biofilm infection is readily accessible, substantial elimination of the biofilm can be feasible. Multiple treatments can be useful to obtain a desired attrition of a particular biofilm.

Also, the treatment processes of the invention can be controlled to be non-damaging to host tissue or to cause only modest, acceptable damage compatible with the seriousness of the infection. This is unlike the process described by Dodick et al. which comprises fracturing the tissue.

Similarly, it is contemplated that the inventive treatment processes can be performed with little, if any, pain being inflicted on the host mammal. In the case of severe or persistent biofilm infections, higher intensity shockwave dosages, which can cause minor discomfort or modest pain, may be acceptable.

At sensitive treatment sites, or in other situations where more gentle treatments are desired, less frequent repetition rates or pressure pulses below shockwave intensity can be employed. For gentle treatments, single pulses at desired intervals, or pulse repetition rates in the range of from about 1 to about 10 Hz, or other desired patterns of repetition, or mild conditions, can be employed, if desired.

In some embodiments of the practice of the inventive biofilm treatment process, the distal port of the shockwave applicator from which shockwaves or other mechanical pulses are output can be translated across the biofilm during the application of mechanical shockwaves. Such translation can be effected by linear movement of the shockwave applicator relatively to the biofilm, by relative rotational movement, or by combinations of the two. Varying the rate of translation or the pattern of translation, or both, provides a surgeon or other operator a useful parameter for controlling the intensity of application. For example, the shockwave applicator can be reciprocated back and forth, with or without rotational movements in juxtaposition to the target biofilm and can output shockwaves in a directional beam so that the directional shockwave beam sweeps back and forth across the target biofilm, ablating the target biofilm progressively with each sweep. If desired, the requisite manipulations can be visually guided according to observation of depletion of the biofilm employing a visual aid such as is described herein.

Other parameters the operator can adjust to help manage a treatment are described elsewhere herein or will be or become apparent to a person of ordinary skill in the art in light of this disclosure. Where helpful to protect local tissue, the biofilm can, if desired, be treated in multiple passes whereby incremental attrition or destruction of the biofilm can be achieved.

As described in the Dodick et al. patents, the passageway in the needle of the Dodick instrument can be used for infusion of saline or for aspiration of saline and tissue. In practicing the present invention, this passageway can be employed for irrigation of the treatment site with saline or other suitable fluid or for aspiration of the fluid and debris, including biofilm remnants produced by application of mechanical shockwaves to the biofilm at the treatment site. In general, it is not anticipated that tissue fragments will be present or aspirated, although in some cases they may be.

In various embodiment of the treatment processes of the invention, the passageway in the shockwave applicator can be employed for aspiration and a separate instrument can be employed for irrigation. In other embodiments of the treatment process of the invention, the passageway in the shockwave applicator can be employed for irrigation and a separate instrument can be employed for aspiration. In further embodiments of the treatment processes of the invention, the shockwave applicator can be provided with passageways for both irrigation and aspiration.

A process embodiment of the invention comprises slow downstream irrigation of the fiber tip to keep it clean and to remove detritus without the use of suction.

The laser energy pulses employed to induce the shockwaves or pressure pulses used in the biofilm treatment processes of the invention can be provided by any suitable laser. For example, as described by Dodick et al., a neodymium-doped yttrium-aluminum-garnet laser ("neodymium-YAG" or "ND:YAG") laser providing light energy at a wavelength of 1,064 nanometers with a pulse width of approximately 8 nanoseconds ("ns" herein) and an absorption coefficient in water of 0.014/mm can be employed. Alternatively, other laser types can be employed, for example, gas lasers or solid lasers.

The laser energy pulses can be provided with any suitable characteristics including pulse width, pulse repetition rate and pulse energy. A pulse width or pulse duration in the range of from about 2 ns to about 20 ns can be employed, for example from about 4 ns to about 12 ns. A pulse rate of from about 0.5 Hz to about 50 Hz, for example from about 1 Hz to about 10 Hz can be employed. Higher pulse rates up to about 100 or 200 pulses per second can be employed, if desired. Any suitable pulse energy can be employed, for example, in a range of from about 2 to about 15 millijoules ("mJ") of energy per pulse. Some embodiments of the invention can employ a pulse duration of from about 8 to about 12 nanoseconds, a repetition rate of from about 2 to about 6 pulses per second and/or an energy per pulse of from about 6 to about 12 millijoules.

In some cases, utilizing such parameters, from about 200 to about 800 shockwave-generating laser energy pulses can be employed to effectively treat a biofilm or a portion of a biofilm addressed by the distal port of the shockwave applicator, without significant tissue or other damage. However, depending upon the area of biofilm to be treated, more or less laser energy pulses may be effective, for example from 5 pulses to 1500 pulses can be employed. For example, smaller treatment sites such as the ethmoid sinus can be effectively treated with a smaller number of pulses, for example less than 200 pulses. Comparably, larger treatment sites, for example a maxillary sinus can be treated with a greater number of pulses, for example 500 or more pulses, and if the area of the site so indicates, more than 800 pulses.

While, as noted herein, the invention is not limited by any particular theory, FIG. 1A helps explain how a pulsed YAG laser, or comparable laser or other energy source, can be employed in embodiments of the present invention to generate high intensity shockwaves of short duration that can be employed to control a biofilm resident in a mammalian host without significant damage to tissue or other host structure supporting or in the vicinity of the biofilm.

FIG. 1A provides a graphic indication of the comparative effects of a number of different therapeutic treatments comprising the application of laser or laser-generated energy to tissue. In general, the therapeutic effect of a particular energy treatment of mammalian tissue and of possible collateral damage will be functions of the nature and quantity of energy delivered and the distribution of the energy over space and time. An excessive concentration of energy in space and time may result in tissue damage, for example, from undue heating.

In FIG. 1A, laser energy application time in seconds and power density in watts/cm$^2$ are plotted on the "X" and "Y" scales respectively while energy density in J/cm$^2$ is plotted on a diagonal scale. All the scales employed are logarithmic so that small graphic differences on each scale may correspond with substantial quantitative differences in the energy parameters depicted. A number of different laser energy technologies is referenced beneath the "X" scale and their approximate time scales are indicated.

As may be seen from FIG. 1A, in general, classical laser technologies such as visible wavelength krypton, argon and long pulse KTP (potassium titanyl phosphate) lasers, as well as longer and shorter infrared lasers, employ relatively low power densities and long application times. These technologies can have useful applications such as for vaporization, coagulation, photodynamic therapy and biostimulation.

More recently developed lasers such as Q-switched lasers and short-pulse KTP lasers and the like employ relatively higher power densities and shorter application times. These technologies can have useful applications such as for photoablation and photodestruction. As shown by an arrow in the upper lefthand corner of FIG. A, a pulsed YAG laser outputting in the infrared, such as can be employed in practicing the present invention, employs a notably high power density, for example, in excess of $10^{12}$ watts/cm$^2$, and a notably short application time, for example measured in nanoseconds or less. Because the higher power density may be applied for a quite short time, the energy density with such a use of a pulsed YAG laser can be comparable with that of classical lasers, namely around $10^2$ joule/cm$^2$, give or take an order of magnitude. The energy density may also depend upon the particular geometry of the application.

The Dodick instrument can be modified as appropriate for use in any one or more process embodiments of the present invention. If desired, the invention can include a shockwave applicator or a range or kit of shockwave applicators adapted for treatment of particular treatment sites. For example, the distal end of the shockwave applicator can be elongated to be received into a subject's nostril for treatment of the upper nasal cavity or can be further elongated for treatment of one or more sinus cavities. For treatment of one or more sinus cavities, the distal end of the shockwave applicator can be sufficiently thin and elongated to be received into the nose and access a desired sinus cavity.

For treatment of cardiac, orthopedic, gynecologic, urologic or other implants, the shockwave applicator can be adapted for catheter delivery of the distal tip of the shockwave applicator to a treatment site via a suitable blood vessel or vessels, for example, an artery. Alternatively, the shockwave applicator can be appropriately modified for subcutaneous delivery, for example, for laparoscopic delivery. The invention includes biofilm treatment processes wherein the shockwave applicator can be delivered via a catheter, or laparoscopically, or in other suitable manner.

In some embodiments of the invention, the shockwave applicator can comprise an inspection fiber to view the treatment site and monitor the progress of the treatment. This capability can be useful for treatment sites which are unexposed or concealed including internal sites such as the upper nose and sinuses and implant surfaces. The inspection fiber can have a distal input end disposable in the vicinity of the applicator needle tip to survey the treatment site and a proximal output end communicating optically with an output device viewable by a surgeon or other operator performing the treatment. The output device can be a video screen, an optic member, or another viewing element. If desired, the inspection fiber can extend through or alongside the shockwave applicator or can comprise a separate device. Also if desired, the shockwave applicator with the inspection fiber can be inserted into a bodily cavity or through an incision to access a treatment site. The inspection fiber can enable the operator to monitor the treatment and manipulate the shockwave applicator accordingly.

In one embodiment of the invention the tip of the shockwave applicator along with an optical fiber can be incorporated into a flexible endoscope suitable for subcutaneous catheter delivery and optical imaging can be employed to enable treated sites to be visually monitored.

In some embodiments of the processes of the present invention, one or more of a number of treatment parameters to facilitate or improve performance of the treatment can be adjusted and improved or optimized for a particular application, for example by manipulation of an appropriate control, or instrument or other device by the surgeon or other operator. These parameters include the orientation, location and/or disposition of the shockwave applicator, the application of saline or other irrigation fluid, the application of suction, and any one or more of the energy parameters employed to generate the applied pressure pulses. The energy parameters include the intensity, frequency, and pulse duration of the pressure pulses.

In the treatment of concealed treatment sites, adjustment of the treatment parameters can be facilitated by providing illumination means at the treatment site to illuminate the treatment site, as described herein. This measure can permit the surgeon, or other operator, to adjust one or more of the treatment parameters according to what he or she sees at the treatment site. Accordingly, some embodiments of the invention comprise illuminating the treatment site.

One embodiment of shockwave applicator useful for practicing the invention is illustrated in the drawings. Other embodiments will be, or become, apparent to a person of ordinary skill in the art in light of the disclosure herein.

Referring to FIG. 1 of the drawings, the distal tip 1 of the shockwave applicator comprises a titanium or stainless steel target 2, an optical fiber 3 which terminates adjacent target 2 and a passage 4 for irrigation fluid. Pulsed laser energy propagated along optical fiber 3 strikes target 2 causing ionization of the target material and inducing a plasma 5. Laser-induced plasma 5 causes a shockwave to be generated and to exit the shockwave applicator through opening 6 in the direction of the arrow 7. Irrigation fluid supplied in the direction of arrow 8 can clean and remove debris from target 2 and the treatment site.

Titanium can be useful as a target material for the purposes of the invention, for its good bio-compatibility and high absorption coefficient with respect to the laser wavelength and for its thermal conductivity. The latter properties can be useful in avoiding propagation of laser energy or heat externally of the shockwave applicator, which could adversely impact sensitive tissue at the treatment site. Other embodiments of the invention can employ stainless steel, zirconium or another suitable target material.

In one embodiment of the shockwave applicator shown in FIG. 1 opening 6 has a diameter of about 0.8 mm, distal tip 1 has a width of about 1.4 mm and the distance between the end of optical fiber 3 and target 2, the fiber-to-target distance, can be in the range of from about 0.7 to about 1.5 mm, for example about 1 mm.

The shockwave applicator shown in FIGS. 2-5 of the drawings, referenced 10, is suitable for application of laser-induced shockwaves to the sinuses and other areas. Shockwave applicator 10 comprises a proximal barrel portion 12 and an elongated distal needle portion 14.

Barrel portion 12 can be suitable for gripping and manipulating the instrument in one hand and can, as shown, be cylindrical and/or be provided with gripping structure, here shown as a plurality of circumferential ribs 16, or can employ other gripping structures, if desired. Barrel portion 12 can have a longitudinal axis (not referenced) along which it has a generally straight, or rectilinear configuration, as shown. Alternatively, barrel portion 12 can be curved, or angled to facilitate its manipulation, or to serve other purposes, if desired.

Proximally, barrel portion 12 has an optical connector 18 to provide an optical fiber connection to a suitable laser source (not shown). Shockwave applicator 10 comprises an optical fiber 20 which extends through shockwave applicator 10 from connector 18 to a point close to the distal tip of shockwave applicator 10, as will be explained. Optical fiber 20 can be a component of shockwave applicator 10 which makes an optical connection at optical connector 18 with another optical fiber leading from the laser source. Alternatively, optical fiber 20 can be a portion of the optical fiber leading from the external laser source which optical fiber portion can be threaded through shockwave applicator 10 via optical connector 18.

A further connector, irrigation connector 22, located at the proximal end of shockwave applicator 10 permits shockwave applicator 10 to be connected to a supply of saline, or other suitable irrigation fluid. An irrigation passageway 24 extends through both barrel portion 12 and needle portion 14 of shockwave applicator 10 to supply irrigation fluid distally to the work site, if desired.

Needle portion 14 of shockwave applicator 10 can be formed integrally with barrel portion 14 or can be permanently or separably attachable thereto. In the embodiment of the invention shown, needle portion 14 has three sections: an elongated proximal section 26, a curved section 28 and a distal tip 30. The several sections of needle portion 14 of shockwave applicator 10 can comprise a integral structure or can comprise separate units permanently or detachably assembled together, if desired. Needle portion 14, or one or more sections thereof can be rigid, or if desired can be flexible to facilitate delivery to the treatment site.

Proximal section 26 is straight in the illustrated embodiment and extends along the longitudinal axis of the barrel portion, but could be curved or angled. Proximal section 26 serves to reach into inaccessible sites, for example to extend through the sino-nasal tract to reach a sinus. Curved section 28 serves to give distal tip 30 a desired orientation to address the treatment site. Proximal section 26 and curved section 28, as illustrated, have approximately constant cross-sectional shapes along their lengths but could be tapered in the distal direction, if desired, or have other variations in their cross-sectional shapes along their lengths.

Distal tip 30 outputs the treatment phases to the treatment site. In the illustrated embodiment, the configuration of curved section 28 can be such as to orient distal tip 30 at an angle to the perpendicular to the longitudinal axis of shockwave applicator 10 suitable for treatment of a sinus region or other desired treatment site. For example, distal tip 30 can be employed to address any one of the maxillary, ethmoid, sphenoid and frontal sinuses. The angle can be in the range of from about 40° to about 60°, for example about 50°, or can have another desired value.

As shown in FIG. 5, distal tip 30 comprises a short straight section of shockwave applicator 10 having a generally triangular cross-section. Distal tip 30 comprises a generally flat upper surface 32 abutted by a lefthand target surface 34 and a righthand surface 36 each of which extends along distal tip 30 and meets upper surface 32 at an acute angle.

Target surface 34 of distal tip 30 can be flat or slightly convex and comprises the surface on which the laser beam output from optical fiber 20 impinges. The material of distal tip 30 at target surface 34 desirably can be selected to facilitate generation of a shockwave when impinged by the laser beam. For this purpose, all or a part of distal tip 30, including target surface 34, can be formed of a suitable ionizable material, for example a metal such as stainless steel, titanium or zirconium. Desirably, distal tip 30 can be constructed so that little or no clinically significant heat is generated externally of distal tip 30 in a way that could be damaging to tissue at the treatment site. This can be done by constituting distal tip 30 in the vicinity of target surface of sufficient heat conductive material as to form a heat sink. Furthermore, it can be desirable to avoid extraneous laser energy escaping distal tip 30 and impinging on tissue by employing for target surface 34 a material having a high absorption coefficient with respect to the laser wavelength, for example, titanium, stainless steel, zirconium or the like.

Optical fiber 20 terminates at any suitable location where it can output a laser beam to strike or impinge lefthand surface 34 so as to generate a shockwave. For example, optical fiber 20 can terminate at the distal end of curved section 28 of needle portion 14 of shockwave applicator 10. This termination is not shown in the drawings. The distally terminal end of optical fiber 20 desirably can be oriented to direct the laser beam on to lefthand surface 34 to generate a shockwave. For example, the optical fiber can terminate at a modest acute angle to the axis of distal tip 30 and direct the output laser beam toward the end of lefthand surface 34.

Righthand surface 36 can be somewhat concave and can provide an alternative target surface, if desired, which is employable with minor reconfiguration of the terminal end of optical fiber 20 to direct the laser beam on to righthand surface 36 rather than on to lefthand target surface 34. If desired, righthand surface 36 can be employed as an alternative laser beam target surface providing, with its different topography a modified shockwave pattern compared with that generated by lefthand surface 34. In another embodiment of the invention, lefthand and righthand surfaces 34 and 36 have similar topographies and the one can be utilized when the other becomes worn.

Desirably, during shockwave generation, irrigation fluid can be delivered to flow coaxially to the fiber distal surface plane to preventing debris accumulating at the light-emitting fiber surface, which could cause damage to or breakage of the fiber. The irrigation fluid can also flow across the laser target surface, if desired, and can exit shockwave applicator 10 along either or both of surfaces 34 and 36 as appropriate. For this purpose, irrigation passageway 24 can have one or two irrigation fluid outlets (not shown) at the distal end of curved section 28 of needle portion 14 of shockwave applicator 10, or in another suitable location, if desired. Also, irrigation fluid supplied through shockwave applicator 10 can be used to irrigate the treatment site, if desired.

In one embodiment of the treatment method of the invention, when the laser is activated, pulses of laser light are output from optical fiber 24 and impinge on the ionizable material of the lefthand surface 34 of distal tip 30 causing heating, ionization and the generation of a shock wave which may have a pattern such as illustrated schematically by reference numeral 38. In the embodiment shown, shockwave pattern 38 can generate forwardly of shockwave applicator 10 with an expanding front in a direction angled downwardly from the axis along distal tip 30. The configuration of shockwave applicator 10 can impede propagation of shockwaves in the opposite direction, helping to concentrate the energy in the direction of the expanding front.

Such a pattern is believed useful for treatment of sinus and other relatively small areas and facilitates concentration of the energy in the shockwave pulses on the targeted biofilm. Desirably, the shockwave pattern can be concentrated within a limited geometric volume in front of shockwave applicator 10 so as to project the energy forwardly so that it can be directed toward the target treatment site rather than dispersing in all directions. Other shockwave patterns 38 can be employed as will be apparent to those skilled in the art.

The embodiment of shockwave applicator 10 shown in FIG. 6 is generally similar to that shown in FIGS. 2-5 with the difference that a modified curved section 128 is employed which has a greater curvature so that distal tip 30 extends along a line at an angle closer to the perpendicular to the longitudinal axis of barrel portion 12 of shockwave applicator 10. This angle can be in the range of from about 10° to about 25°, for example about 18°, or can have another desired value.

Shockwave applicator 10 can be disposable, being used for one or possibly more treatments of a single patient. Alternatively, shockwave applicator 10 can be reusable and sterilizable. Shockwave applicator 10 can have any suitable dimensions. Some embodiments of shockwave applicator 10 have an overall length, as viewed in FIG. 3, of from about 150 mm to about 250 mm, for example about 200 mm, barrel portion 12 and needle portion 14 being in proportion.

Barrel portion 12 can have any suitable transverse dimensions that are comfortable and efficient for the user, for example a physician. The transverse dimensions of needle portion 14 can be adapted to the intended target anatomy. For sinus applications, the largest transverse dimensions of those parts of needle portion 14 that are intended to enter the sino-nasal tract to access one or more sinuses desirably is relatively small for example not more than about 5 mm. In some embodiments, the largest transverse dimension of distal tip 30, of curved section 28 and optionally also of proximal section 26 of needle portion 14 is not more than about 3 mm. This dimension can be 2 mm or less, for example in the range of from about 1 mm to about 1.5 mm.

The thinness of needle portion 14 can be helpful when inserting shockwave applicator 10 into a bodily cavity of a patient to reach inaccessible sites such as a sinus site. In these embodiments of the invention, optical fiber 20 is desirably sufficiently thin to be accommodated within a thin needle portion 14, having a diameter, for example, in the range of from about 0.1 mm to about 1 mm (from about 100 µm to about 1,000 µm). Some embodiments of optical fiber 20 can have a diameter in the range of from about 0.2 mm to about 0.5 mm (from about 200 µm to about 500 µm).

Usefully, to treat inaccessible sinus, otological or other sites, needle portion 14 can include a distal length of at least about 20 mm, for example from about 30 mm to about 50 mm, which has a cross-section sufficiently small to be received into the nose and the sino-nasal tract.

Any suitable laser system can be employed to provide laser energy to optical fiber 3 of the shockwave applicator illustrated in FIG. 1. One example of a suitable laser system comprises a Nd:YAG laser operating in the infrared at a wavelength of 1064 nm, which can be Q-switched to provide high intensity energy pulses, if desired. Using an optical fiber 3 of diameter 283 µm, the Nd:YAG laser system can be employed to generate pulsed laser energy with a pulse length of about 4 ns (nanoseconds), a frequency of from about 1 to about 10 Hz and with an energy of from about 10 to about 15 mJ. If desired, the laser system can include a control computer and a video display to monitor performance.

One treatment process utilizing the illustrated shockwave applicator comprises inspecting a treatment site harboring a biofilm or otherwise diagnosing a condition appropriate for treatment by a laser-induced shockwave process according to the invention and determining a suitable treatment protocol. For example, distal tip 30 of the illustrated shockwave applicator is then inserted into the bodily cavity constituted by the patient's nostril, through the naris, and is manipulated to address the internal bodily site to be treated, for example a sinus.

When shockwave applicator 10 is properly positioned, the laser source is activated to supply a desired dosage of laser pulses along optical fiber 20. In one embodiment of the invention the treatment site is positioned in front of laser target surface 34 with respect to the laser or optical fiber 20. The laser energy strikes target surface 34 of distal tip 30, generating shockwave 38 which is applied to the treatment site. Shockwave 38 is generated in the fluid medium, air, irrigation fluid or the like, on the same side of the target surface as is impinged by the laser beam and in some cases will have a direction of propagation which is approximately in the direction of reflection of the laser beam from the target surface, or in the direction the laser beam would have been reflected if not absorbed by the target.

Desirably, during treatment, the distance from the closest point of distal tip 1 to the treatment site is in the range of from about 0.5 mm to about 10 mm, for example from about 1 mm to about 5 mm, and so far as is practical, the distance is maintained, for example by suitable manipulation of the shockwave applicator by the user.

It is contemplated that the effect of the laser-induced shockwaves impacting on biofilm present at the target site, including biofilm adhered to tissue at the treatment site, will be to attenuate, disrupt, disperse or weaken the biofilm or to cause the biofilm to lose its integrity or lose adherence to its substrate or to cause one or more pieces to break away. Multiple ones of these results may occur and the biofilm may be destroyed partially or entirely. Dosages can be increased and treatments can be repeated to increase biofilm attrition, if desired. Dosages can be controlled to limit collateral tissue damage or inflammation which it is believed can be controlled to be little or modest, or not visibly apparent, employing dosages such as are described herein.

Subsequently to, or concurrently with, application of laser-induced shockwaves, irrigation fluid can be supplied via irrigation connector and irrigation passageway 24 to remove debris including biofilm detritus, if generated, and clean distal tip 30 and the treatment site.

If desired, an endoscope (not shown) can be employed with the illustrated shockwave applicator to view the treatment process and treatment site and the endoscope may comprise a video camera or other suitable optics. The endoscope can be used simultaneously with the use of the illustrated shockwave applicator to apply shockwaves or it can be employed to inspect the treatment site before and after treatment. Also, if desired, the illustrated shockwave applicator can be modified for endoscopic delivery to the treatment site.

If desired, the laser-induced shockwave treatments of the invention can be accompanied by or followed by local or systemic administration of an antibiotic to limit or control possible infection associated with dispersal of the targeted biofilm.

Some examples of antibiotics that can be employed include one or more compounds selected from the group consisting of cefmetazole, cefazolin, cephalexin, cefoxitin, cephacetrile, cephaloglycin, cephaloridine, cephalosporin c, cephalotin, cephamycin a, cephamycin b, cephamycin c, cepharin, cephradine, ampicillin, amoxicillin, hetacillin, carfecillin, carindacillin, carbenicillin, amylpenicillin, azidocillin, benzylpenicillin, clometocillin, cloxacillin, cyclacillin, methicillin, nafcillin, 2-pentenylpenicillin, penicillin n, penicillin o, penicillin s, penicillin v, chlorobutin penicillin, dicloxacillin, diphenicillin, heptylpenicillin, and metampicillin. Other suitable antibiotics will be or become apparent to a person of ordinary skill in the art.

Treatment systems according to the invention can include a shockwave applicator such as the illustrated shockwave applicator and a laser system selected and tuned to supply appropriate laser energy to the illustrated shockwave applicator. The treatment apparatus can also include associated computing and display equipment and, optionally, an endoscope for treatment site inspection, process monitoring and/or instrument delivery.

As stated, the second step of a biofilm treatment process according to the invention can comprise applying an antimicrobial dosage of light and the biofilm treatment systems can comprise an appropriate light applicator.

The term "light" is used herein to include visible wavelength radiation, as well as near-visible infrared radiation or ultraviolet radiation, useful for the purposes of the invention, in the range of from about 200 nm up to about 1500 nm in wavelength. Monochromatic or polychromatic light sources can be employed. Other radiant energies, such as heat or RF energy, can be included with the applied light energy radiation, provided they do not cause adverse side effects, for example undue heating of tissue. In one embodiment of the invention, at least 50 percent of the applied radiant energy is visible or near infrared light.

Usefully, antimicrobial treatments employed in the practice of the invention can comprise a microorganism-reducing light dosage having an energy and duration sufficient to reduce the microorganism population yet which is insufficient to cause tissue damage or pain to the treated subject.

Suitable light energy can be provided for an antimicrobial treatment by employing a laser, laser diode, light-emitting diode or other light source capable of outputting light at a wavelength or wavelengths in a range of from about 200 nm to about 1500 nm. If desired the light energy may be output in a range of from about 400 nm to about 1200 nm. In one embodiment of the invention, at least 80 percent of the energy is output in a visible wavelength range of from about 400 nm to about 700 nm.

In some embodiments of the invention, the light energy does not include, and can substantially exclude ultraviolet wavelengths. For example in these embodiments, no more than about 10 percent, desirably no more than about 5 percent, or 1 percent, of the light energy is at wavelengths below about 380 nm.

If desired, the methods of the invention can include the applying of a colorant to the treatment site and optionally to one or more other sites whence biofilm components may be dispersed, to photosensitive the target microorganism to complementary visible wavelengths in the dosage of light to be applied. Colorant application can comprise crushing a colorant applicator containing a frangible capsule of colorant fluid and applying colorant to the target structures with the colorant applicator or in another suitable manner.

In embodiments where a colorant is employed, the method can use a laser source to generate the attenuating radiation which supports output of light radiation at a wavelength in a range of from about 400 nm to about 700 nm, the colorant and radiation wavelength being selected for absorption of the radiation by the colorant. For example the colorant can be methylene blue or toluidine blue and relatively red or orange, complementary light of wavelength of about 630-660 nm may be employed. Using rose Bengal, complementary wavelengths of about 400-500 nm can be employed.

In some embodiments of the invention, no colorant is employed. Useful antimicrobial treatments for these embodiments can employ a laser source capable of generating infrared light at a wavelength in a range of from about 850 nm to about 950 nm.

The microorganism-reducing light can be applied at any suitable energy level and duration, which parameters can be determined by routine experimentation. One example is at an energy level of from about 1 mW to about 200 mW for a duration sufficient to deliver from about 0.2 to about 20 Joules.

In another example, the microorganism-reducing radiation is applied at from about 10 mW to about 100 mW for a duration sufficient to deliver from about 2 to about 10 Joules.

Antimicrobial light treatment of subjects can be effected by a medical professional or other suitable individual, employing a light applicator with any suitable light energy-generating system or light source. For example, a laser having a maximum power input of about 3 watts and supporting light output of from about 900 to about 940 nm can be employed. The laser can be used with a SMA connector and an optical fiber having a diameter of about 400 to about 800 micron, for example about 600 micron. The optical fiber can have any suitable tip for example a tip having an external diameter of about 1.5 mm, and a diffuser of length of about 10-20 mm. A fiber length of 0.5 to 1.5 meters can be convenient. Some other specifications can comprise an optical fiber of from about 100 to about 1200 micron diameter, a tip having an external diameter of from about 0.5 to about 2 mm, and a diffuser of length of from about 3 to about 30 mm.

A useful antimicrobial treatment duration can be in the range of from about 30 seconds to about 15 minutes. The invention includes embodiments wherein the antimicrobial treatment duration is from about 1 minute to about 10 minutes, for example from about 2 to about 5 minutes.

The method of the invention can comprise providing a subject with a personal light applicator to enable the subject to self-administer an antimicrobial treatment in place of or as an adjunct to professionally applied antimicrobial treatment. An example of one useful device for this purpose is a BioNase (trademark) phototherapy system supplied by Syro Technologies R & D Ltd., of Jaffa, Israel. This product is a pocket-sized unit with dual output outputting red light at 6 mW per nostril timed for a treatment duration of about 4.5 minutes. Such a device can include a nasal clip, clampable to the septum, to support the device for self-administration.

One example of the antimicrobial treatment method comprises applying a liquid colorant to a treatment site, for example the nasal cavity of the subject, and possibly also one or more sinus cavities, inserting a light transmissive nasal dilator through a naris of the subject to dilate the nostril of the subject, inserting a light output member into the nasal dilator and activating a light source to deliver light through the nasal dilator to the anterior nasal cavity of the subject. The light output member can comprise a fiber optic tip communicating with a remote light source, a support-mounted light-emitting diode, or other suitable light source.

In one example of the practice of the invention, the antimicrobial treatment is carried out to effect a microorganism count reduction of at least about 50 percent. In another embodiment, the antimicrobial treatment is carried out to effect a microorganism count reduction of at least about 80 percent. The antimicrobial treatment can be carried out to effect a microorganism count reduction of at least about 90 percent or of at least about 95 percent. The invention includes embodiments wherein the microorganism count reduction effected is higher than 95 percent, for example in the range of from 98 to 100 percent. A desired reduction can be effected in a single antimicrobial treatment, or as a result of multiple antimicrobial treatments having cumulative effect.

The antimicrobial treatment can be repeated with any desired frequency, for example, within about 1 to 7 days, or otherwise as will be apparent to a person of ordinary skill in the art.

Referring to FIGS. 7 and 8, the light applicator here shown, reference 58, is suitable for partial insertion into a nasal or other bodily cavity and comprises a generally cylindrical hand piece 60 on which a light tube 62 is supported as a distal extension thereof. Nasal light applicator 58 further comprises a sheathed optical fiber 64 which extends longitudinally through hand piece 60 and into light tube 62 and a light source (not shown), for example a laser, a laser diode, a light-emitting diode, a gas discharge lamp, a flash lamp, an intense pulsed light or another suitable light source, to supply light to optical fiber 64 in a controllable manner.

Hand piece 60 can be embodied as a disposable unit, if desired which can be dedicated to a single patient or other treatment subject. Some embodiments of hand piece 60 are releasably attachable to optical fiber 64, so that, if desired, each patient can be treated with a new or dedicated unit embodying essentially all the surfaces likely to be contacted by the patient or the physician, technician or other user. If desired, hand piece 60 can be provided in a variety of sizes for patients with different anatomies. The dimensions and other structural characteristics of nasal light applicator 58 can also be varied to provide units of different functionality, for example a tip-of-the-nose probe, a deep nasal probe or other desired nasal light applicator. Individual hand pieces 60 can be sterilized and sealed in their own wrapper, if desired.

Optical fiber 64 has a portion within light tube 62 from which the sheathing has been removed to provide a length of exposed fiber 66 from which light transmitted along optical fiber 64 can radiate laterally, and in other directions, to be applied to the treatment site.

Light tube 62 comprises a transparent or translucent outer cover 67 and a cylindrical diffuser 68 disposed within outer cover 67 and around exposed fiber 66. Cylindrical diffuser 68 can have a transparent or translucent appearance and can be formed of frosted or whitened or other suitable diffusing material. In one embodiment of the invention, cylindrical diffuser 68 completely surrounds exposed fiber 66 to diffuse light emitted from exposed fiber 66 and scatter it laterally of light tube 62. If desired, outer cover 67 can be disposable. One or more outer covers 67 can be packaged with hand piece 60, if desired, or they can be packaged separately.

Both outer cover 67 and cylindrical diffuser 68 desirably have good light transmissivity for the treatment light and can be formed of any suitably transmissive material, such as acrylic or polycarbonate plastic, or glass. Optionally, cylindrical diffuser 68 can have a light transmissivity which is limited to a selected waveband and can, if desired, be a light filter, for example an orange or red filter.

Cylindrical diffuser 68 can be supported in any suitable manner. For example, cylindrical diffuser 68 can have a base portion 70 supported by hand piece 60. Optionally, cylindrical diffuser 68 can have a tip portion 72 which tapers distally and supports the distal tip 74 of optical fiber 64 and can, if desired have a small aperture or recess to receive and locate distal tip 74 of optical fiber 64. If desired, for example for structural stability, tip portion 72 of optical fiber 64 can be sheathed. Also, base portion 70, or other relevant hand piece structure, can be reflective to block light traveling proximally and redirect it distally.

In one embodiment of the invention, a shield or mask (not shown) is provided around, or partially replacing, cylindrical diffuser 68 to limit the output light pattern to a desired window, for example, a selected radial angle.

In some embodiments of the invention, light tube 62 is dimensioned to be receivable into a patient's nostril and can be provided in different sizes according to an intended patient's anatomy. To this end, hand piece 60 can include a number of outer covers 67 for light tube 62 which have different diameters and lengths. Some exemplary lengths of outer cover 67, measured to shoulder 76 of hand piece 60, can be in a range of from about 5 mm to about 30 mm, desirably from about 10 mm to about 20 mm. Some exemplary diameters of outer cover 67, can be in a range of from about 3 mm to about 20 mm, desirably from about 5 mm to about 10 mm.

Usefully, outer cover 67 can be configured and dimensioned to function as a nasal dilator, for example by selecting its dimensions, in relation to a particular patient so that the patient's nostril will be appropriately dilated, as described herein, when light tube 62 is inserted into the patient's nostril. In one embodiment of the invention, the patient's nostril is significantly distended when light tube 62 is sufficiently inserted to illuminate the interior of the nostril, including the nasal vestibule.

Externally, the embodiment of hand piece 60 shown has an ergonomic structure enabling it to be easily and conveniently manipulated, for example in the manner of a pen or pencil, by gripping it between the thumb and forefingers. Other suitable shapes or configurations of hand piece 60 will be apparent to a person of ordinary skill in the art. Some optional external structural features of hand piece 60 include a smooth beveled shoulder 76, recesses 78 and elongated, slender overall proportions.

Shoulder 76 of hand piece 60 can abut the patient's nostril and prevent over-insertion of light tube 62 into the nostril, in some cases. Optionally, and depending upon the particular patient, shoulder 76 and light tube 62 may adequately dilate the patient's nostril without use of a separate instrument such as nasal dilator 12. Recesses 78 can comprise small depressions suited to be engaged by the tips of a user's thumb and/or fingers, to facilitate control and manipulation of hand piece 60.

Internally, hand piece 60 has a hollow longitudinal cavity 80 to accommodate optical fiber 64 to which hand piece 60 can be secured by suitable clamping or other means. In some useful embodiments of the invention, hand piece 60 is releasably attachable to optical fiber 64. This capability can permit the tension in the fiber to be adjusted and allow for replacement of worn or damaged fiber either by moving hand piece 60 along optical fiber 64 to a new length of fiber, or by complete replacement of the fiber. In another embodiment of the invention, hand piece 60 is permanently attached to optical fiber 64.

Various mechanical arrangements for releasably attaching hand piece 60 to optical fiber 64 will be or become apparent to a person of ordinary skill in the art. For example, handpiece 60 can be formed in two sections, namely a body section 82 and an end section 84 which are screwed together by means of threads 86, the sections meeting joining at a band 88. Screwing the sections together brings thread 86 on body section 82 into engagement with a ball clamp 87. Ball clamp 87 is resiliently compressible and has an axial opening (not shown) to receive optical fiber 64. As body section 82 and end section 84 are tightened together, the thread 86 on body section 82 bears down on ball clamp 87 compressing it around, and locking it on to, optical fiber 64 desirably without shifting optical fiber 64 axially.

Optionally, end section 84 of hand piece 60 can have a short end sleeve 90 through which optical fiber 64 can be inserted into hand piece 60. Desirably, end sleeve 90 can frictionally grip optical fiber 64 to act as a strain relief device preventing external strains being transmitted to ball clamp 82 and other downstream structures.

To further stabilize the mounting of hand piece 60 on optical fiber 64, a number, for example three or four, of circumferentially arranged and radially extending contoured guide ribs 92 can be provided in body section 82 of hand piece 60 towards its distal end. Guide ribs 92 can center optical fiber 64, and optionally can slidingly engage it with limited pressure, helping to position optical fiber 64 in light tube 62.

Outer cover 67 of light tube 62 can be attached to hand piece 60 in any suitable manner, desirably in a removable manner. For example, outer cover 67 can be a snap fit into a recess in the forward or distal end of body section 82 of hand piece 60, and can, if desired be locked in place by rotational engagement of detent such as detents 94, providing a quickly connected fitting that is easily manipulated by a busy physician or other operator.

Body section 82 and end section 84 of hand piece 60 can be manufactured in any suitable manner from appropriate materials, for example by molding from plastics materials. For example, the more complex body section 82 can be fabricated from polycarbonate or the like, and the simpler end section 84 can also be fabricated from polycarbonate or from a polyolefin, or an acrylic polymer or copolymer or the like.

In one method of use of nasal light applicator 58 a physician, an infection control nurse clinician, or other appropriate technician, or operator, unwraps a new or sterilized hand piece 60 and selects a light tube outer cover 67 of appropriate size for the patient to be treated. If necessary, an existing outer cover 67 can be removed from the hand piece 60 and one of appropriate size can be quickly snapped into place. Alternatively, the outer cover 67 of appropriate size can be fitted to hand piece 60 after the latter is assembled to optical fiber 64, which assembly is described below.

The hand piece 60 is assembled with optical fiber 64 by first unscrewing end section 82 from body section 84 of hand piece 60 to sufficiently to open ball clamp 87. Optical fiber 84, with a section of sheathing removed to provide a suitable length of exposed fiber 66 at its distal end, is then manually threaded through end sleeve 90, through ball clamp 87 and between guide ribs 92 to emerge into light tube 62 where its distal tip can be advanced to engage with tip portion 72 of cylindrical diffuser 68. End section 84 is then screwed into body section 82 to lock ball clamp 87 onto optical fiber 64 and provide a secure, integral assembly. Disassembly of hand piece 60 from optical fiber 84 can be quickly accomplished by reversing the assembly procedure. Employing some embodiments of the invention, both assembly and disassembly can readily be accomplished without the use of tools.

The proximal end of optical fiber 64 is then connected to a light source, if not already connected, and nasal light applicator 58 is ready for use.

To apply a light treatment to the patient's nostril, the physician or other user, the physician can grip hand piece 60 in one hand and gently insert light tube 62 through the naris into the patient's nostril with sufficient penetration to provide a desired field of illumination within the nostril. The depth of penetration can for example be about 8 mm to 12 mm in pediatric cases or from about 15 mm to about 20 mm in adult cases.

After insertion of light tube 62, the physician switches the light source causing light to radiate from exposed fiber 66 and diffuse through cylindrical diffuser 68 to illuminate the interior of the patient's nostril with light of the selected wavelength or waveband. For example, nostril can be illuminated coaxially and homogeneously with the illumination in the direction of the mechanical axis of the fiber being prevented. If desired, colorant can be applied inside the nostril before applying the light treatment.

In some useful embodiments of the invention the ergonomic design of hand piece 60 enables it to be conveniently gripped, permitting the physician or other holder to effect a carefully controlled insertion of light tube 62 into the patient's nostril, with fine movements to position hand piece 60, as desired for one or more light treatments, for example for treatments at different depths of penetration or different angles. Hand piece 60 is held in place in the patient's nostril for the duration of each treatment, for example for from about 1 to about 3 minutes.

When one nostril has been adequately treated hand piece 60 is moved to the other nostril and a similar treatment is performed. If desired, outer cover 67 can be removed and a new outer cover 67 can be fitted to hand piece 60 for treating the patient's other nostril to avoid cross-contaminating the nostrils. Optionally, the two outer covers 67 can be identified with respect to the nostril for which they have been used and used for the same nostril in future treatments of the particular patient. Thus, it is possible to dedicate a hand piece 60 to a particular patient and to dedicate one or more outer covers 67 to each of the patient's individual nostrils. Both hand piece 60 and the outer covers 67 can be re-used in future treatments of the patient and disposed of at the end of a course of treatment, or when no longer serviceable. A new, or newly sterilized, hand piece 60 is employed for the next patient.

By employing a slightly oversized outer cover 67, stretch the internal skin of the nostril can be stretched as light tube 62 is introduced into the nostril, exposing the hair within the nostril and baring the inner lining the skin of the nostril, to facilitate illumination of the inner lining of the nasal skin for desired period of time. A tight fit of light tube 62 within the nostril can help keep the tip of the applicator instrument in a fixed position.

In summary, nasal light applicator 58, as illustrated in FIGS. 7-8, can be embodied as a disposable unit to be used for a single patient to control contamination from patients carrying pathogenic bacteria. Since the distal end of the hand piece 60 is inserted into the patient's nostril, a disposable cover is provided which can be replaced easily between nostrils and potentially used in multiple applications in the same patient.

While nasal light applicator 58 has been described with reference to the example of the application of treatments by a medical professional, it will be understood that the invention includes embodiments of nasal light applicator 58 that are suitable for home use or for self administration.

Some non-limiting examples of the practice of the processes of the invention in vitro will now be described which illustrate methods and materials that can be employed in practicing the claimed invention. In vitro results that can be obtained will also be described.

EXAMPLE 1

Destruction of a Biofilm

A sample biofilm is treated with laser-generated shockwaves employing a pulsed Nd:YAG laser at a wavelength of 1064 nm. The laser output energy is between about 8 mJ and about 12 mJ. The laser is pulsed using passive Q-switch pulsing with a pulse length between about 4 ns and about 8 ns. The laser energy is delivered to the biofilms using a shockwave applicator intended for cataract surgery such as is described in Dodick U.S. Pat. No. 5,906,611. As described in the Dodick patent, in the shockwave applicator, an optical fiber tip outputting laser pulses is aimed at a titanium target producing plasma and generating a shockwave.

Distally, the shockwave applicator employed comprises a disposable needle or probe instrument in the form of a hollow metal 1.2 mm diameter tube coupled with an optical fiber of diameter about 300 μm at one end and with a 0.7 mm opening at the other end. The laser beam propagates axially inside the tube and hits a titanium target, positioned adjacent and above the opening at the tip of the probe to output shockwaves through the opening. The shockwave applicator has a passageway for irrigation fluid which outputs adjacent the shockwave opening.

To apply shockwaves to the biofilm, the shockwave applicator can be moved toward the samples and then maintained at a distance of about 5 mm to 10 mm from the biofilm while operating the laser to generate shockwaves. The shockwaves can be initiated by a series of low energy laser pulses in a slow stream of irrigation liquid. A 488 nm laser is used to excite the yellow fluorescent protein and 488 nm and 543 nm laser lines are used to excite the propidium iodide treated samples.

During treatment of the biofilm with the Nd:YAG laser a time-lapse imaging function is used to capture images in the transmitted mode. Image rendering is effected by confocal stacks and time series are rendered using Imaris BITPLANE (trademark) image rendering software.

During exposure to the shockwaves generated by the Nd:YAG laser each biofilm can be seen to oscillate in response to laser pulses directed at the biofilm from a distance in excess of about 10 mm. As the shockwave applicator approaches the target area to a distance of about 5 mm to about 10 mm away, while generating laser-induced shockwaves, in most cases, some of the biofilm is disrupted and detached immediately. Generally, the rest of the biofilm detaches after exposure to a number of pulses, i.e. about 10 to about 20 shockwaves. Following the clearing of the biofilm from its host surface, the attached and previously protected bacteria can be seen floating in the liquid medium. The applied shockwave treatment clearly disrupts the biofilms and exposes the protected microorganisms. The exposed biofilm bacteria are accordingly rendered more susceptible to antibiotics or other anti-infective therapeutic modalities.

No visible damage to the biofilm support structure resulting from the shockwave treatments may be apparent.

EXAMPLE 2

Two Step Treatment of Biofilm

A number of biofilms of *S. aureus* Xen 31, a stable bioluminescent clinical methicillin-resistant *Staphylococcus aureus*, construct, are grown in a 96 well microtiter plate for 48 hours. The study includes the following seven trials:
a) control;
b) ciprofloxacin alone (at 3 mg/L, an established minimum inhibitory concentration);
c) shockwave treatment alone;
d) near infrared laser alone
e) shockwave treatment and ciprofloxacin;
f) shockwave treatment plus near infrared laser treatment; and
g) shockwave treatment, near infrared laser and ciprofloxacin.

The shockwave treatment is carried out with a Q-switched Nd-YAG laser set with a frequency of 1 pulse per second at a wavelength of 1,064 nm and output energy for the laser system of from about 8 to about 12 mJ. Each biofilm treated is exposed to 10-20 pulses of shockwave placed in each of the tested wells. The near infrared treatment is carried out with a 940 nm diode constant output near infrared laser applied for a duration of 180 seconds with an energy level of 3 W with a distance between the well and the probe set constantly to cover the entire well diameter of 0.7 cm diameter providing a power density of about 7.8 W/cm$^2$. Given the duration of 180 seconds, the total energy density is about 1400 joule/cm$^2$.

The results are evaluated with a biophotonic system from IVIS Technologies for determining live bacteria concentrations, and by determining optical density ("OD"), to determine total bacteria concentrations.

Some results which can be obtained are shown below where the percentages given are percentage reductions in bacterial colony count in the samples, as determined, respectively, by optical density measurement or by the IVIS instrument.

| Trial | OD | IVIS Instrument |
|---|---|---|
| a) control | | |
| b) ciprofloxacin alone | 44% | 58% |
| c) shockwave treatment alone | 15% | 8% |
| d) near infrared laser alone | 20% | an increase |

-continued

| Trial | OD | IVIS Instrument |
|---|---|---|
| e) shockwave plus ciprofloxacin | 79% | 81% (P < 0.05) |
| f) shockwave plus near infrared | 43% | 88% (P < 0.05) |
| g) shockwave plus near infrared plus ciprofloxacin | 81% | 85% (P < 0.05) |

The confidence level is shown parenthetically for the more significant results.

These results suggest that the antibiotic ciprofloxacin alone provides a partial reduction in bacterial density. Trials with shockwaves or infrared light alone provided little or no reduction. With a combination of the shockwave treatment and near infrared treatment, but no antibiotic, there is a 43% reduction in OD (P<0.05), which is much greater than either energy treatment alone, suggesting that the biofilm may be disrupted. Also, the combined two step energy treatment exhibits a surprising 88% reduction (P<0.05) in the live bacteria count. In contrast, ciprofloxacin alone resulted in a decrease of only 28% of total live cells, comprising biofilm remaining attached and disrupted planktonic cells, and 58% of biofilm cells (both P>0.05). Ciprofloxacin in combination with shockwave treatment and shockwave treatment plus the near infrared laser shows a decrease of over 60% in total live biomass and over 80% of biofilm cells, which is significantly greater than ciprofloxacin alone (P<0.05).

Biofilms are becoming regarded as an integral part of chronic rhinosinusitis pathology. Bacteria in biofilm communities may display significantly greater resistance to traditional antimicrobial therapies than their planktonic (mobile) counterparts. Shockwave treatments such as are described in Example 1 can successfully disrupt a biofilm in vitro, and can apparently remove the biofilm in first step. Example 2 illustrates two step processes which can include killing the biofilm.

While the invention is not limited by any particular theory, the two step bacteria killing process can be explained by hypothesizing that the first step converts the bacteria from the biofilm forming state to a dispersed and detached floating state wherein a second strike can be inflicted. The second strike can comprise a relatively weak diffuse, infrared laser, or an antibiotic or both infrared light and an antibiotic.

A possible explanation for the slight significance of the ciprofloxacin containing trial versus the laser only trial is a temperature rise to over 44 C.° rendering the antibiotic less active. Such a temperature rise may be a possible explanation for the bactericidal effect of the laser.

A person of ordinary skill in the art will understand that in vivo results may be different from the in vitro results described herein.

The ability to clean and remove biofilm from complex, delicate implant materials, without damage, which can be provided by embodiments of the inventive processes and systems has useful application in a variety of fields including, for example, for cleaning biofilm-contaminated cardiac implants and associated devices and materials.

As has been referenced herein, the invention includes embodiments wherein the described laser-induced shockwave technology is coupled with endoscopic techniques to facilitate the visualization of, and access to, in vivo biofilms, facilitating the treatment of deeper tissue infections.

Another embodiment of the invention comprises a process for treating biofilms comprising employment of a laser-induced shockwave generating instrument for cellular level ablation or "shaving" of a biofilm resident in vivo. For example, the process can comprise selectively removing a first layer of biofilm with an initial shockwave application, followed by one or more additional shockwave applications to remove additional layers of the biofilm. Each shockwave application can comprise traversing the shockwave across the biofilm by suitably manipulating the instrument. The biofilm can comprise invasive pathogens and the initial shockwave application can expose the invasive pathogens or other microorganisms for destruction by additional shockwaves, or in other desired manner. Subsequent shockwave applications can similarly expose layers of microorganisms deeper in the biofilm. If desired, any suitable antimicrobial therapy can be employed for treating the bacteria or other microorganisms exposed and dispersed after disruption of the biofilm.

A further embodiment of shockwave applicator according to the invention comprises illumination means or an illumination device to illuminate the target area to facilitate monitoring of the treatment. If desired, the illumination means can comprise an illumination fiber having a proximal light input end communicating with a light source and having a distal light output end locatable in the vicinity of the treatment site to illuminate the treatment site. The illumination fiber can be movable with the shockwave applicator. For example it may be a component of the shockwave applicator or it can be a separate device. Illumination means not only can be usefully employed to illuminate concealed treatment sites but may also be useful for treatment of biofilms resident at exposed treatment sites.

Other shockwave or pressure pulse generators that can be employed in the practice of the present invention include piezoelectric, for example piezoceramic, devices, spark discharge devices, electromagnetically or inductively driven membrane pressure shockwave generators or pressure pulse generators and generators that employ pressure currents or jets associated with the transport of material. The pressure pulse generator can be disposed in the shockwave applicator or externally in a separate unit connected to the shockwave applicator by a transmission line, if desired.

Such other pressure pulse generators may provide useful shockwaves or pressure pulses for biofilm disruption or attenuation, without use of laser or other photic energy, as will be understood by those skilled in the art.

The energy output of some of the herein described embodiments of shockwave applicator are flexibly controllable and accurate and well suited to treatment of mammalian host resident biofilms. For example, a number of the parameters of such shockwave applicators can be manipulated and varied, including for example, the laser energy and pulse frequency, the optical fiber thickness, the fiber-to-target distance and the geometry of the distal output opening through which the shockwave generates to impinge on a target organ, or other output structure, to vary the output. Any one or more of these and other parameters is, or are, available for adjustment to adapt the applied energy, the energy concentration at the treatment site, the energy duration, the pattern of application and other factors, for any particular treatment. Thus, the invention can provide a user with a flexible treatment process and instrument which can be adapted, without difficulty, to treat biofilms in a variety of locations in a mammalian body.

The processes and systems of the invention employing laser-generated or other shockwave or pressure wave technology can be useful for disruption or other treatment of host-resident biofilms in otolaryngology and other fields. Some embodiments of the invention are contemplated as having safety parameters when employed for biofilm treatment that allow treatments to be effected in close proximity to sensitive and critical anatomical structures, including for example, cranial nerves and large blood vessels. Furthermore, the mechanical nature of the laser generated shockwave that is applied to the biofilm, in some embodiments of the invention avoids the issues of toxicity and acquired resistance commonly associated with high and/or repeated doses of antibiotics.

The foregoing detailed description is to be read in light of and in combination with the preceding background and invention summary descriptions wherein partial or complete information regarding the best mode of practicing the invention, or regarding modifications, alternatives or useful embodiments of the invention may also be set forth or suggested, as will be apparent to one skilled in the art. The description of the invention is intended to be understood as including combinations of the various elements of the invention, and of their disclosed or suggested alternatives, including alternatives disclosed, implied or suggested in any one or more of the various methods, products, compositions, systems, apparatus, instruments, aspects, embodiments, examples described in the specification or drawings, if any, and to include any other written or illustrated combination or grouping of elements of the invention or of the possible practice of the invention, except for groups or combinations of elements that will be or become apparent to a person of ordinary skill in the art as being incompatible with or contrary to the purposes of the invention.

Throughout the description, where processes are described as having, including, or comprising specific process steps, it is contemplated that compositions of the present invention can also consist essentially of, or consist of, the recited components, and that the processes of the present invention can also consist essentially of, or consist of, the recited processing steps. It should be understood that the order of steps or order for performing certain actions is immaterial so long as the invention remains operable. Moreover, two or more steps or actions may be conducted simultaneously.

While illustrative embodiments of the invention have been described above, it is, of course, understood that many and various modifications will be apparent to those of ordinary skill in the relevant art, or may become apparent as the art develops, in the light of the foregoing description. Such modifications are contemplated as being within the spirit and scope of the invention or inventions disclosed in this specification.

The invention claimed is:

1. A two-step mammalian biofilm treatment process comprising:
a first step of dispersing an undesired biofilm present at a treatment site in or on a mammalian host by mechanically disrupting the biofilm, the disrupting comprising applying laser-generated mechanical shockwaves to the biofilm; and
a second step comprising applying an antimicrobial treatment to the mammalian host, the antimicrobial treatment comprising applying an antimicrobial dosage of light to the treatment site, to control possible infection related to the biofilm dispersed in the first step or to residual biofilm at the treatment site;
wherein the second step is performed within a limited time period after the first step.

2. The process according to claim 1 wherein the limited time period is selected from the group consisting of 48 hours, 24 hours, 3 hours, 1 hour, 30 minutes and 10 minutes after the application of laser-generated mechanical shockwaves.

3. The process according to claim 1 wherein the second step comprises diffusing the-antimicrobial dosage of light onto the treatment site and in the vicinity of the treatment site.

4. The process according to claim 3, further comprising applying the-antimicrobial dosage of light to at least one other site on or in the mammalian host subject to material dispersed from the biofilm in the first step.

5. The process according to claim 1 wherein the antimicrobial dosage of light reduces or controls at least one species of the microorganisms in the biofilm.

6. The process according to claim 1 wherein the biofilm comprises matter foreign to the mammalian host and the first step further comprises mechanically disrupting the biofilm.

7. The process according to claim 1 wherein the biofilm is attached to the treatment site and the first step comprises one or more steps selected from the group steps consisting of: directing the mechanical shockwaves toward the biofilm at the treatment site; oscillating the biofilm by the application of the mechanical shockwaves; and tearing one or more pieces of the biofilm away from residual biofilm at the treatment site or from the treatment site by applying the mechanical shockwaves.

8. The process according to claim 1 wherein the biofilm comprises one or more infectious microorganisms selected from the group consisting of bacteria, fungi, protozoa, archaea, algae and microscopic parasites, an antibiotic-resistant microorganism, methicillin-resistant *Staphylococcus aureus*, antibiotic-resistant *Staphylococcus aureus*, antibiotic-resistant alpha-hemolytic streptococci, antibiotic-resistant *Streptococcus pneumoniae*, antibiotic-resistant *Haemophilus influenzae*, antibiotic-resistant coagulase-negative Staphylococci, *aspergillus, candida* and *penicillium* families, *mycoplasma, alternaria, Chlamydia*, antifungal-resistant *aspergillus*, antifungal-resistant *candida* and antifungal-resistant *penicillium* families, antifungal-resistant *mycoplasma, alternaria* and antifungal-resistant *Chlamydia*.

9. The process according to claim 1 wherein the first step comprises impinging a pulsed laser beam on to an ionizable target to generate non-convergent pulses of mechanical shockwaves.

10. The process according to claim 9 wherein the first step comprises pulsing the laser beam impinged on the target with one or more pulse characteristics selected from the group consisting of a pulse width in the range of from about 2 ns to about 20 ns, a pulse rate of from about 0.5 Hz to about 200 Hz, a pulse energy in a range of from about 2 mJ to about 15 mJ of energy per pulse, and a fiber-to-target distance in the range of from about 0.7 to about 1.5 mm.

11. The process according to claim 1 wherein the antimicrobial treatment comprises one or more steps selected from the group of steps consisting of: applying to the biofilm a dosage of light having a wavelength of from about 400 nm to about 1500 nm; applying to the biofilm a dosage of light having a wavelength in the range of from about 600 nm to about 1200 nm; applying to the biofilm a dosage of light having a wavelength in the range of from about 800 nm to about 1200 nm and the light dosage is applied without applying colorant or photosensitizer material to the treatment site; applying to the biofilm a dosage of light having a wavelength in the range of from about 850 nm to about 950 nm and the light dosage is applied without applying colorant or photosensitizer material to the treatment site; and applying to the biofilm a dosage of light having a wavelength in the range of from about 400 nm to about 700 nm together with a photosensitizer material selected to absorb the dosage of light.

12. The process according to claim 1 wherein the light dosage is applied at an energy of from about 1 mW to about 200 mW for a duration sufficient to deliver from about 0.2 to about 20 Joules of energy.

13. The process according to claim 1 wherein the light dosage is applied at an energy intensity of from about 10 mW to about 100 mW for a duration sufficient to deliver from about 2 to about 10 Joules.

14. The process according to claim 1 wherein the treatment site comprises a sinus or posterior nasal site, the biofilm being present at the sinus or posterior nasal site and the second step comprises flooding or both nasal cavities with a diffuse antimicrobial dosage of light.

15. The process according to claim 14 wherein the second step comprises applying a photosensitizing colorant to the anterior nasal cavity to sensitize infectious microorganisms present in the anterior nasal cavity to the microorganism-reducing light.

16. The process according to claim 15 comprising applying the light dosage of microorganism-reducing light to each nasal vestibule of the mammalian host.

17. The process according to claim 15 comprising inserting a light-diffusing nasal dilator through a naris of the mammalian host to dilate the nostril of the mammalian host and delivering the light dosage through a fiber optic tip located within the nasal dilator and through the nasal dilator to the anterior nasal cavity of the mammalian host.

18. The process according to claim 1 wherein the treatment site comprises one or more treatment sites selected from the group consisting of: otolaryngological sites; middle ear cavities; pharyngal sites; tonsillar sites; dental sites; periodontal sites; toenails; fingernails; wound closure devices and materials; sutures; implant sites; cardiac implant sites; endovascular implant sites; orthopedic implant sites; gynecological implant sites; intrauterine device sites; urologic implant sites and urinary catheter sites.

19. The process comprising repetition of a process according to claim 1 at one or more intervals of from about 1 to about 7 days.

20. The process of claim 1, wherein the disruption caused by the mechanical shockwaves further comprises tearing one or more pieces of the biofilm away from residual biofilm at the treatment site.

21. The process of claim 1, wherein the disruption caused by the mechanical shockwaves further comprises tearing one or more pieces of the biofilm away from the treatment site.

22. The process of claim 1, wherein the disruption caused by the mechanical shockwave further comprises breaking up the biofilm into pieces.

23. The process of claim 1, wherein the disruption further comprises breaking up the biofilm into planktonic cells.

24. The process of claim 1, wherein the disruption caused by the mechanical shockwave further comprises substantially dislodging the biofilm from its host structure without causing visible damage to the host structure.

25. The process of claim 24, where the host structure is body tissue of a patient.

26. The process according to claim 1 wherein the antimicrobial treatment comprises applying to the biofilm a dosage of light having a wavelength in the range of from about 800 nm to about 1200 nm.

27. The process according to claim 26, wherein the light dosage is applied without applying colorant or photosensitizer material to the treatment site.

28. The process of claim 1, wherein the antimicrobial treatment comprises applying to the biofilm a dosage of light having a wavelength in the range of from about 850 nm to about 950 nm.

29. The process according to claim 28, wherein the light dosage is applied without applying colorant or photosensitizer material to the treatment site.

\* \* \* \* \*